US012263860B2

(12) United States Patent
Jung et al.

(10) Patent No.: US 12,263,860 B2
(45) Date of Patent: *Apr. 1, 2025

(54) SYSTEM FOR PREVENTING DRUNK DRIVING AND METHOD FOR CONTROLLING THE SAME

(71) Applicant: HYUNDAI MOBIS CO., LTD., Seoul (KR)

(72) Inventors: Yu Jin Jung, Uiwang-Si (KR); Yeon Su Kim, Gunpo-Si (KR); June Seung Lee, Yongin-Si (KR); Chang Won Lee, Seoul (KR)

(73) Assignee: HYUNDAI MOBIS CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/590,156

(22) Filed: Feb. 28, 2024

(65) Prior Publication Data

US 2024/0199057 A1 Jun. 20, 2024

Related U.S. Application Data

(63) Continuation of application No. 17/877,306, filed on Jul. 29, 2022, now Pat. No. 11,945,461.

(30) Foreign Application Priority Data

Aug. 5, 2021 (KR) .................. 10-2021-0103019
Aug. 5, 2021 (KR) .................. 10-2021-0103021

(Continued)

(51) Int. Cl.
*B60W 50/14* (2020.01)
*B60K 28/06* (2006.01)

(Continued)

(52) U.S. Cl.
CPC ........... *B60W 50/14* (2013.01); *B60K 28/063* (2013.01); *B60W 10/06* (2013.01); *B60W 40/08* (2013.01);

(Continued)

(58) Field of Classification Search
CPC ...... B60W 50/14; B60W 10/06; B60W 40/08; B60W 50/10; B60W 50/12;

(Continued)

(56) References Cited

U.S. PATENT DOCUMENTS

2005/0065447 A1* 3/2005 Lee ................... A61B 5/4806
600/529
2007/0144812 A1 6/2007 Stewart et al.

(Continued)

FOREIGN PATENT DOCUMENTS

EP 2100763 A1 9/2009
JP 2005096663 A 4/2005

(Continued)

OTHER PUBLICATIONS

Extended European Search Report issued on Jan. 2, 2023 in corresponding European patent application No. 22187731.9.

*Primary Examiner* — Ryan W Sherwin
(74) *Attorney, Agent, or Firm* — NovoTechIP International PLLC

(57) ABSTRACT

Disclosed are a drunk driving prevention system and a method of controlling the system that includes a sensor module measuring a alcohol content in the exhaled breath of a driver during a breath-checking of the driver and a control module configured to check the intoxication state of the driver from the alcohol content measured by the sensor module to determine whether the breath-checking is complete and block an engine start when the breath-checking fails, wherein the control module includes a check unit (Continued)

displaying breath-checking guide information through a display unit and the check unit displays the breath-checking guide information based on an engine start input of the driver.

10 Claims, 12 Drawing Sheets

(30) Foreign Application Priority Data

| | | |
|---|---|---|
| Aug. 5, 2021 | (KR) | 10-2021-0103023 |
| Aug. 5, 2021 | (KR) | 10-2021-0103030 |

(51) Int. Cl.
    *B60W 10/06*      (2006.01)
    *B60W 40/08*      (2012.01)
    *B60W 50/10*      (2012.01)
    *B60W 50/12*      (2012.01)
    *G01N 33/497*      (2006.01)
    *G06V 20/59*      (2022.01)
    *G06V 40/16*      (2022.01)

(52) U.S. Cl.
    CPC ............ *B60W 50/10* (2013.01); *B60W 50/12* (2013.01); *G01N 33/4972* (2013.01); *G06V 20/597* (2022.01); *G06V 40/161* (2022.01); *B60W 2040/0836* (2013.01); *B60W 2050/146* (2013.01); *B60W 2420/403* (2013.01); *B60W 2540/24* (2013.01)

(58) Field of Classification Search
    CPC ... B60W 2040/0836; B60W 2050/146; B60W 2420/403; B60W 2540/24; B60K 28/063; B60K 35/29; B60K 35/65; B60K 35/654; B60K 2360/161; B60K 2360/197; B60K 2360/21; B60K 2360/741; B60K 35/00; B60K 35/22; B60K 35/28; G01N 33/4972; G06V 20/597; G06V 40/161; A61B 5/0077; A61B 5/097; A61B 2010/0009; A61B 2010/0087; A61B 2503/22; A61B 5/082; A61B 5/18; A61B 5/4845

See application file for complete search history.

(56) References Cited

U.S. PATENT DOCUMENTS

| | | | |
|---|---|---|---|
| 2009/0090577 A1* | 4/2009 | Takahashi | G01N 33/4972 340/576 |
| 2009/0164069 A1 | 6/2009 | Yanagisawa | |
| 2010/0043524 A1* | 2/2010 | Takata | G01N 33/4972 73/23.3 |
| 2014/0135598 A1* | 5/2014 | Weidl | A61B 5/48 600/300 |
| 2014/0165697 A1* | 6/2014 | Mochizuki | G01N 33/4972 73/23.3 |
| 2015/0081134 A1 | 3/2015 | Burger | |
| 2015/0204844 A1* | 7/2015 | Nothacker | G06V 40/20 73/23.3 |
| 2015/0212063 A1* | 7/2015 | Wojcik | G06V 40/167 340/576 |
| 2015/0233897 A1* | 8/2015 | Hok | G01N 33/4972 73/23.3 |
| 2015/0325240 A1* | 11/2015 | Li | G10L 15/08 704/231 |
| 2016/0243939 A1 | 8/2016 | Kawasaki et al. | |
| 2017/0096145 A1 | 4/2017 | Bahn | |
| 2018/0074081 A1* | 3/2018 | Wakana | H04N 23/51 |
| 2018/0116579 A1 | 5/2018 | Omi | |
| 2019/0248237 A1 | 8/2019 | Albakri | |
| 2020/0074155 A1* | 3/2020 | de Paula | G06V 40/174 |
| 2022/0358788 A1 | 11/2022 | Morisaki et al. | |

FOREIGN PATENT DOCUMENTS

| | | |
|---|---|---|
| JP | 5348457 B2 | 11/2013 |
| KR | 101705968 B1 | 2/2017 |
| WO | 2022025811 A1 | 2/2022 |

\* cited by examiner (a) facial mask is worn   (b) facial mask is not worn (a) default mode   (b) facial mask wear mode (a) normal breath check attempt (b) abnormal breath check attempt
(unauthorized object is present)

SYSTEM FOR PREVENTING DRUNK DRIVING AND METHOD FOR CONTROLLING THE SAME

CROSS-REFERENCE TO RELATED APPLICATIONS

The present application is a continuation of co-pending U.S. application Ser. No. 17/877,306 filed on Jul. 29, 2022, which claims the benefits of priority to Korean Patent Application No. 10-2021-0103019, filed Aug. 5, 2021, Korean Patent Application No. 10-2021-0103021, filed Aug. 5, 2021, Korean Patent Application No. 10-2021-0103023, filed Aug. 5, 2021, and Korean Patent Application No. 10-2021-0103030, filed Aug. 5, 2021, the disclosure of which is incorporated herein by reference in their entirety.

TECHNICAL FIELD

The present disclosure relates to a system for preventing drunk driving and a method of controlling the system for preventing drunk driving, and more particularly, to a technology for providing a guide display for the drunk driving prevention system.

BACKGROUND

Attempts are being made to employ a drunk driving prevention system in a vehicle to prevent the drunk driving.

In this regard, Korean Patent No. 10-705968 discloses a technology for checking whether a driver is intoxicated using biometric information obtained by bodily contact of the driver with an alcohol tester and unlocking the shift lever of a vehicle only when the driver is not intoxicated, thereby preventing drunk driving of the vehicle.

In addition, Japanese Unexamined Patent Publication No. 2005-096663 discloses a technology for determining whether a driver is intoxicated using the exhaled breath of the driver and cutting off electricity for starting a vehicle when it is determined that the driver is intoxicated, thereby preventing the drunk driving.

In addition, Japanese Patent No. 5348457 discloses a driver monitoring device provided with a camera for photographing the driver and an alcohol detection device, and an interlocking device blocking engine start when alcohol is detected in the driver's exhaled breath by the alcohol detection device. In particular, Japanese Patent No. 5348457 discloses a device configured to allow engine start only when the identity of the driver is verified based on a plurality of photographs taken by the camera immediately before and after an alcohol detection test by the alcohol detection device.

The drunk driving prevention system installed in the vehicle is rarely used in practice while the drunk driving prevention system needs to be activated each time the driver gets in the vehicle such that the driver is forced to spend time waiting for messages from the system, thereby posing a major obstacle to the wide use of the drunk driving prevention system.

SUMMARY

The present disclosure focuses on enhancing the convenience of drivers by selectively providing a guide display relating to a drunk driving prevention system under certain conditions to raise the utilization of the drunk driving prevention system.

According to the present disclosure, the drunk driving prevention system includes a sensor module measuring the alcohol content in the exhaled breath of a driver during a breath-checking of the driver and a control module configured to check the intoxication state of the driver from the alcohol content measured by the sensor module to determine whether the breath-checking is complete and block an engine start when the breath-checking fails, wherein the control module includes a check unit displaying alcohol test guide information through a display unit and the check unit displays the alcohol test guide information based on the engine start input of the driver.

The check unit determines that the driver intends to drive and displays the alcohol test guide information when an engine start input by the driver is an engine start-on input for driving the vehicle and determines that the driver does not intend to drive and does not display the alcohol test guide information when the engine start input by the driver is an electronic device-on input for activating electronic devices.

The check unit may not display the alcohol test guide information while the vehicle is driving.

According to the present disclosure, the drunk driving prevention system further includes a camera capturing images including the face of the driver seated in the driver's seat and a storage unit storing image information captured by the camera, wherein the control module may include an image processing unit processing the image information captured by the camera, and when the current driver returns to the driver's seat within preset reference time from the end of the previous driving, the check unit may compare the image information processed by the image processing unit with the image information of the driver stored in the storage unit during the previous driving to check whether the driver is the same, and may not display the alcohol test guide information when the driver enters the engine start input if it is determined that the driver is the same.

The control module may include a determination unit comparing an alcohol content measured by the sensor module with a reference alcohol content to check the intoxication state of the driver and a vehicle control unit transmitting a control command to activate an engine start block device when the determination unit determines that the measured alcohol content of the driver exceeds the reference alcohol content and that the driver is intoxicated.

The display unit may display vehicle state information transmitted from the vehicle controller, and the vehicle state information is divided into safety feature information and convenience feature information. The display unit may stop displaying the alcohol test guide information and display the safety feature information instead when the display of the safety feature information is requested while the alcohol test guide information is displayed and display the convenience feature information after the display of the alcohol test guide information is terminated when the display of the convenience feature information is requested while the alcohol test guide information is displayed.

According to the present disclosure, the drunk driving prevention system may further include a camera capturing images including the face of the driver seated in the driver's seat, wherein the control module may determine whether the driver wears a facial mask based on the image captured by the camera and check the intoxication state of the driver to activate the engine start block device of the vehicle, the control module may only complete the breath-checking when the breath volume of the driver supplied into the sensor module is equal to or greater than a preset first reference breath volume and commands the sensor module to measure alcohol content in the exhaled breath of the driver, and the control module may reset the reference breath volume for completing the breath-checking downward to a second reference breath volume when it is determined that the driver wears the facial mask.

The control module may include a check unit determining whether the driver wears the facial mask from the image captured by the camera and determining whether the breath-checking is complete based on the breath volume of the driver supplied into the sensor module, the determination unit comparing the alcohol content measured by the sensor module with the reference alcohol content to check the intoxication state of the driver, and the vehicle control unit transmitting a control command to activate the engine start block device when the determination unit determines that the measured alcohol content of the driver exceeds the reference alcohol content and that the driver is intoxicated According to the present disclosure, the display unit may display guide information to the driver as a facial mask wear mode is entered and may output guide information for the driver to be positioned close to an inlet of an inhaling unit of the sensor module when the facial mask wear mode is entered.

The camera may transmit the captured image information to the image processing unit of the control module in real-time, the image processing unit may generate a frame for the facial position of the driver and transmits the image information matching the frame to the display unit, the display unit may output the image information matching for the frame in real-time, and the image processing unit may provide the frame enlarged at a preset proportion when the facial mask wear mode is entered.

The control module may command the sensor module to increase rotation speed of a fan installed on the inlet side of an inhaling port when the facial mask wear mode is entered.

The control module may close the windows of the vehicle and switch the vehicle into the inside aide mode once the breath-checking starts and may switch vehicle state as per the vehicle information before the breath-checking after the breath-checking is completed.

According to the present disclosure, the drunk driving prevention system may further include the camera capturing images including the face of the driver seated in the driver's seat, wherein the check unit of the control module may commands the notice device to provide a first image capture notice when the image capture by the camera is requested during a breath-checking or while the vehicle is driving, and the control module may command the camera to capture images after the first image capture notice is provided.

The check unit may omit the first image capture notice provided while the vehicle is driving as per the driver's setting. When the driver setting specifies that the first image capture notice is not required while the vehicle is driving, the image capture by the camera may be performed without providing the image capture notice even when the image capture by the camera is requested.

According to the present disclosure, the drunk driving prevention system may further include the camera capturing images including the face of the driver seated in the driver's seat, wherein the control module may check whether the breath in the captured image matches the breath pulled into the sensor module based on comparison result between the first estimated breathing period calculated from the change in the mouth of the driver during the breath-checking in the captured image and a second estimated breathing period determined by the change in the breath volume pulled into the sensor module to complete the breath-checking.

The control module may include an image analysis unit configured to process and analyze the captured image. The image analysis unit may check whether an unauthorized object other than the driver is present in the captured image, and the control module may not complete the breath-checking when the presence of an unauthorized object is detected.

The control module may include a seat sensing unit sensing the presence of a passenger and a position change of the passenger from the seat sensors in passenger seat and rear seat, and the control module may not complete the breath-checking when a position change of the passenger is detected.

According to the present disclosure, a control method of the drunk driving prevention system includes receiving the engine start input from the driver and determining whether or not to display the alcohol test guide information based on the engine start input from the driver.

In the determining of whether or not to display alcohol test guide information, it may be determined that the driver intends to drive and the alcohol test guide information is displayed when the engine start input of the driver is an engine start-on input for driving a vehicle, while it may be determined that the driver does not intend to drive and the alcohol test guide information is not displayed when the engine start input from the driver is an electronic device-on input for activating the electronic devices.

The check unit may not display the alcohol test guide information while the vehicle is driving.

According to the present disclosure, the drunk driving prevention system and the display control method using the system minimize the occurrence of unrequired pop-ups and help block unrequired exposure to the pop-ups and save time and effort required in removing the related check process and the pop-ups thereof, thereby enhancing the convenience of the vehicle occupants. In addition, whether the driver wears a facial mask is determined based on the image captured by the camera provided in the vehicle, and distinct breath-checking and intoxication determination logic are applied depending on the wear or non-wear of the facial mask, thereby ensuring effective utilization of the drunk driving prevention system.

In addition, according to the present disclosure, the occupants may properly recognize the time of image capture by the camera of the drunk driving prevention system in various situations, thereby blocking the storage and exposure of inappropriate image information.

In addition, according to the present disclosure, the drunk driving prevention system and method provide an enhanced breath-checking method that may neutralize various attempts to avoid the breath-checking by bypassing the drunk driving prevention system.

DETAILED DESCRIPTION

A drunk driving prevention system and a display control method using the system according to various embodiments of the present disclosure will be described with reference to accompanying drawings hereinafter.

Figure 1:
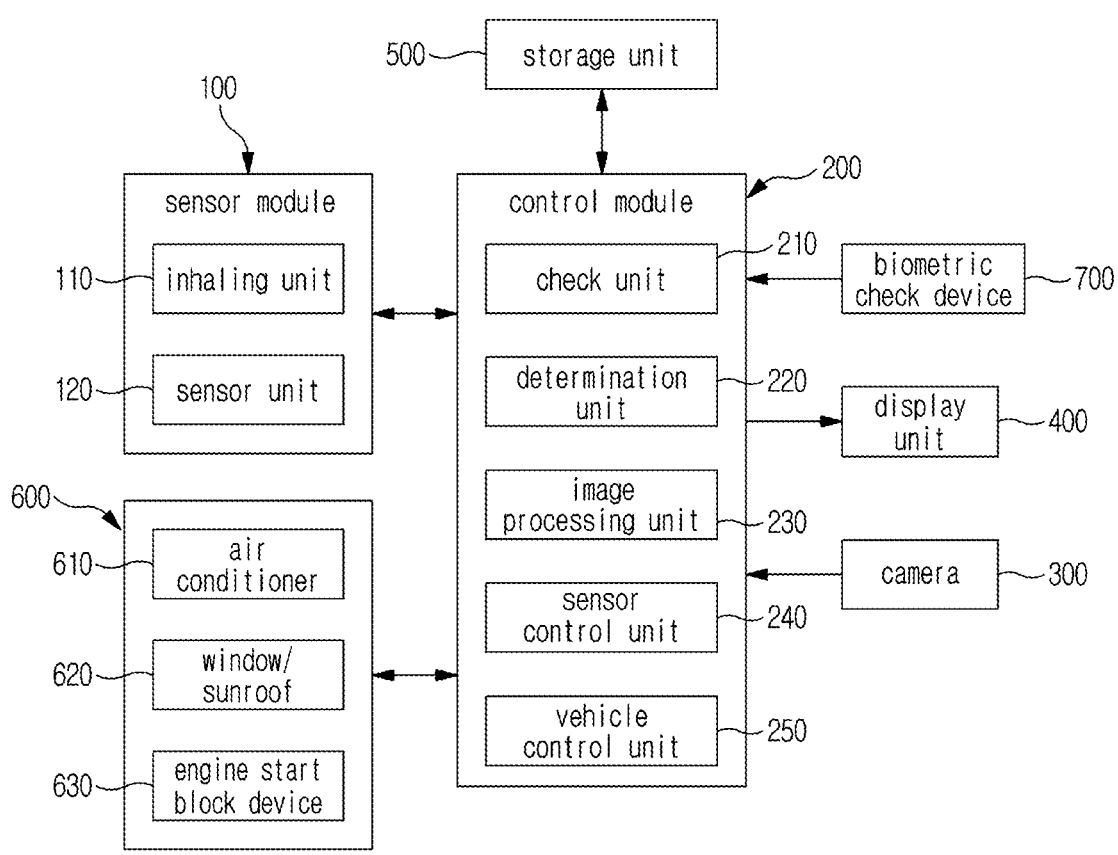
FIG. 1 is a block diagram of a drunk driving prevention system according to an embodiment of the present disclosure.

FIG. 1 is a block diagram of a drunk driving prevention system according to an embodiment of the present disclosure.

As illustrated in FIG. 1, according to a preferred embodiment of the present disclosure, the present disclosure may include a camera 300 capturing images including the face of a driver seated in a driver's seat, a sensor module 100 measuring the alcohol content in the exhaled breath of the driver, and a control module 200 checking the identity of the driver based on the images captured by the camera 300 and checking the intoxication state of the driver from the alcohol content measured by the sensor module 100 to activate an engine start block device 630 of the vehicle.

The camera 300 may be installed in the vicinity of the driver's seat inside the vehicle and photograph the driver seated in the driver's seat. The camera 300 may transmit the captured image information to the control module 200 and the control module 200 may process a subsequent process such as checking the identity of the driver based on the captured images of the driver.

In addition, according to a preferred embodiment of the present disclosure, the drunk driving prevention system may include a storage unit 500 configured to store various information such as image information captured by the camera 300 and alcohol content information measured by the sensor module 100 and a display device 400 configured to display to a driver various information relating to the breath-checking process. The display device may be a display device in a vehicle, and preferably may be a navigation device having a display unit such as AVN (audio, video, navigation) device or a cluster.

In particular, according to the preferred embodiment of the present disclosure, the drunk driving prevention system may be a system that includes a control module and a sensor module to implement a bypass mode in a narrow sense or a system that includes configurations such as the camera, a storage unit, and a display device in a broad sense. However, configurations such as a camera and a storage unit are not ruled out even in the system in a narrow sense and the system may be implemented by interlocking a camera, a storage unit, and a display unit provided in a vehicle system with the control module and sensor module.

According to a preferred embodiment of the present disclosure, the sensor module 100 may pull the breath of a driver and measure the alcohol content in the exhaled breath of the driver. To this end, the sensor module 100 may include an inhaling unit 110 pulling exhaled breath of the driver and a sensor unit 120 provided with an alcohol content measurement sensor measuring the alcohol content in the exhaled breath of the driver.

The inhaling unit 110 may be installed at a position where the breath exhaled by the driver may be easily pulled and may preferably be installed in the vicinity of the cluster, steering wheel, or center fascia.

In particular, the inhaling unit 110 of the sensor module 100 is provided with a fan driven by a motor, and the air intake may be increased or decreased by controlling the rotation speed of the fan. The fan is installed in the inlet portion of the inhaling unit 110, and the motor for driving the fan may be controlled by a control unit of the sensor module 100 or a sensor control unit 240 of the control module 200.

In addition, the sensor unit 120 may measure the breath volume pulled into the inhaling unit 110 and the alcohol content in the pulled air. In this regard, the sensor may include a carbon dioxide sensor for measuring the breath volume and an ethanol sensor for measuring the alcohol content in the exhaled breath of the driver. In addition, the sensor module may include an optical sensor configured to optically measure the alcohol content in the breath.

The carbon dioxide sensor may measure the carbon dioxide volume in the breath of the measuring target. Whether the driver provides sufficient breath volume to ensure credibility in measuring the alcohol content is checked based on the breath volume of the driver measured by the carbon dioxide sensor.

The measured breath volume information and alcohol content information may be transmitted to the control module 200. Accordingly, the control module 200 may compare the measured breath volume information and the alcohol content information with a preset reference alcohol content to determine whether the driver is intoxicated and whether the driver may be allowed to drive.

According to a preferred embodiment of the present disclosure, the drunk driving prevention system may include a display unit for displaying various information. The display unit 400 may be a vehicle display device present within the field of view of the driver such as a display on a vehicle cluster or a display of an audio, video, navigation (AVN) system, or a separate display may be provided.

For example, when the display unit is a large-screen cluster, the screen of the cluster may be divided into the center, right, and left portions and breath-checking information and the like may be output in a preset area within the divided screens.

In addition, when the display unit is an AVN system, the screen may be divided into right and left portions such that the breath-checking information may be displayed on the left portion close to the driver, or the information may be displayed on the entire screen.

The display unit 400 may display various information that the driver needs to be informed of in the process of operating the drunk driving prevention system. In particular, the information on the breath-checking process may be displayed.

For example, the display unit 400 may display messages relating to the specific information on whether the breath-checking is complete, a request for a repeat breath-checking, a cause of a failure in the breath-checking, and the like when the breath-checking starts.

According to the present disclosure, the drunk driving prevention system may include a storage unit 500. Various information including the image information captured by the camera 300 in the process of breath-checking, alcohol content measurement information as measured by the sensor module 100, and the like may be stored in the storage unit 500. The image information may include the time of image capture, the face of the driver, and the like.

In addition, the image information captured when an abnormality is detected inside the vehicle after the driver gets out of the vehicle may be stored in the storage unit 500. The information stored in the storage unit may be transmitted to a server by a communication module in the vehicle.

In addition, the storage unit 500 may store vehicle information including the open/closed state of windows and the operating state of an air conditioner before the breath-checking starts. In checking the intoxication state of the driver, the breath-checking is preferably performed in the inside air mode with all windows/sunroof 620 closed for accurate measurement so that the control module 200 closes the windows/sunroof 620 and switches the vehicle into the inside air mode once the breath-checking starts. To this end, a vehicle control unit 280 of the control module 200 may transmit a control command to open/close the windows/sunroof 620 or switch between inside and outside air modes of an air circulation device. In addition, the vehicle control unit 280 may close the vehicle doors for the breath-checking.

At this time, the information stored in advance before the breath-checking refers to the information on the surrounding environment set by the driver before checking the intoxication state. Accordingly, after the breath-checking is completed, the control module 200 switches the vehicle state as per the vehicle information stored in the storage unit 500 before the breath-checking so that the in-vehicle device 600 may return to the previous state set by the driver. However, since opening the vehicle door is not possible, it is preferable that the door state is not stored in the storage unit 500.

According to the preferred embodiment of the present disclosure, the drunk driving prevention system may further include a biometric check device 700 for checking the identity of the driver. The biometric check device 700 is for checking the driver information and may include a biometric identification device configured to check the fingerprint or iris information of the driver.

The storage unit 500 may store the biometric information of a specific driver, and the check unit 210 may compare the stored biometric information with the biometric information of the current driver obtained through the biometric check device 700 to process the identification.

In addition, the control module 200 may be connected to other configurations in the system such as the sensor module 100, camera 300, display device 400, and storage unit 500 through a communication interface and control the entire system according to the information transmitted from these configurations.

The control module 200 may include a check unit 210, a determination unit 220, an image processing unit 230, a sensor control unit 240, and a vehicle control unit 250. The respective configurations included in the control module 200 are classified according to functions performed by the control module 200 and the respective configurations constituting the control module 200 are not necessarily separated physically. Configurations other than the check unit 210, that is, the determination unit 220, the image processing unit 230, the sensor control unit 240, and the vehicle control unit 250 are configurations provided as illustrative examples to describe the general functions of the drunk driving prevention system. Any form that may implement a drunk driving prevention system even when some of these configurations are missing may be employed as the control module of the present disclosure. In addition, the respective configurations in the control module may communicate with each other.

According to the preferred embodiment of the present disclosure, the control module 200 is a controller configured to perform various functions such as breath-checking, intoxication state determination, and vehicle control and may include a processor executing calculations and a memory in which an algorithm to perform functions of the processor is stored to performs these functions. In addition, the control module 200 may be modularly provided with the check unit 210, the determination unit 220, the sensor control unit 240, and the vehicle control unit 250. In addition, the sub-configurations of the control module 200 are illustrative examples. The control module 200 may perform the same or equivalent functions while communicating with other vehicle controllers, in which case some sub-configurations may be removed or replaced.

Among the basic configurations of the control module, the check unit 210 may oversee the breath-checking process, and the determination unit 220 may compare the alcohol content measured by the sensor module 100 with the reference alcohol content to check the intoxication state of the driver.

The check unit may check whether the driver is seated from the information provided by a device such as a weight sensor of the driver's seat or a camera 300 photographing the driver's seat and check the identity of the driver from the images captured by the camera 300. In addition, the check unit 120 may provide guide information relating to the breath-checking process through the display unit 400 and determine whether the breath-checking is complete based on the breath volume of the driver provided to the sensor module 100.

Here, the breath-checking refers to a process in which the breath of the driver is pulled, the alcohol content in the exhaled breath of the driver is measured by the sensor module 100, and whether the driver is intoxicated is determined according to the alcohol content measured by the sensor module. In addition, that the breath-checking is complete means that the process in which the control module determines that the alcohol content in the exhaled breath of the driver is within a reference value and that the driver is fit for driving is completed.

For example, once the check unit 210 starts the breath-checking, the sensor module 100 measures the alcohol content in the exhaled breath of the driver, the information on the measured alcohol content is transmitted to the control module 200, and the determination unit 220 of the control module 200 may compare the alcohol content measured by the sensor module 100 with the reference alcohol content to check the intoxication state of the driver.

When the comparison result shows that the measured alcohol content of the driver exceeds the reference alcohol content and it is determined that the driver is intoxicated, the determination unit 220 may determine that the driver may not drive (fail the breath-checking) due to intoxication, and the vehicle control unit 250 of the control module 200 may activate an engine start block device 630. In this regard, the engine start block device 630 refers to a device that blocks the starting of the vehicle to disable the vehicle. For example, the engine start block device may be a device that cuts off ignition power. In contrast, when the measured alcohol content of the driver is within the reference alcohol content, it may be determined that the driver is fit for driving and that the breath-checking is completed.

In addition, the check unit displays guide information based on the current state of the system and measurement result through the display unit when the breath-checking process relating to the alcohol test by the drunk driving prevention system is performed.

For example, the check unit may issue guide information such as 'WAIT', 'READY', 'APPROVED', and 'DISAPPROVED' through the display unit in the breath-checking process. Here, 'WAIT' refer to a standby state of the sensor module for hardware initialization, sensor preheating, and the like. In addition, 'READY' refers to a state in which the driver may perform the breath-checking and a state in which the position of the sensor module is displayed to guide the breath-checking. In addition, 'APPROVED' refers to a situation in which the measured alcohol content is equal to or less than the threshold value and the driver passes the breath-checking, and 'DISAPPROVED' refers to a situation in which the measured alcohol content in the breath of the driver exceeds the threshold value and the driver fails the breath-checking. On the other hand, when insufficient breath volume of the driver is input during the breath-checking, a guide message for adjusting the breathing position of the driver such as 'RETRY' instruction may be displayed. All information provided through the drunk driving prevention system, including a guide relating to the breath-checking process is collectively referred to as alcohol test guide information.

In addition, the check unit may variably display alcohol test guide information according to the engine start state of the vehicle in displaying alcohol test guide information.

Basically, the alcohol test is to be performed each time the driver attempts to start the engine. However, when the same driver gets seated in the driver's seat again within a certain time or when the driver does not intend to drive, it is preferable to do without the pop-up on the display for the alcohol test. In addition, when a normal breath-checking is completed and the vehicle is driving, the alcohol test guide information provided by the drunk driving prevention system is unrequired.

Accordingly, according to the preferred embodiment of the present disclosure, the drunk driving prevention system checks whether the driver is a recently validated driver or whether the person seated in the driver's seat does not intend to drive and does not display a guide to the breath-checking process in such exceptional circumstances, thereby enhancing the convenience of passengers. In addition, according to the preferred embodiment of the present disclosure, the display unit does not display alcohol test guide information while the vehicle is driving. For example, if the breath-checking is completed deceptively to avoid the alcohol test and the vehicle has started driving, the drunk driving prevention system does not display alcohol test guide information even when the deceptive breath-checking is detected, thereby prioritizing safe driving. In addition, even if the drunk driving prevention system continuously operates while the vehicle is driving, the related guide information is not displayed while the vehicle is driving in this embodiment.

In this regard, a specific example in which the check unit selectively provides alcohol test guide information will be described later with reference to FIGS. 2 and 3.

In addition, the drunk driving prevention system may include an image processing unit 230, a sensor control unit 240, and a vehicle control unit 250.

The image processing unit 230 is for processing the image information captured by and received from the camera 300 into the image information that the control module 200 needs. The sensor control unit 240 is for controlling the sensor module and may control the rotation speed of the fan of the sensor module 100, the sensitivity of the sensor module 100, and the like. The vehicle control unit 250 may transmit to other in-vehicle devices 600 control commands on the vehicle doors, windows/sunroof 620, an air conditioner 610, an engine start block device 630, and the like.

A specific example of a display control method of the alcohol test guide information of the drunk driving prevention system will be described with reference to FIGS. 2 and 3.

Figure 2:
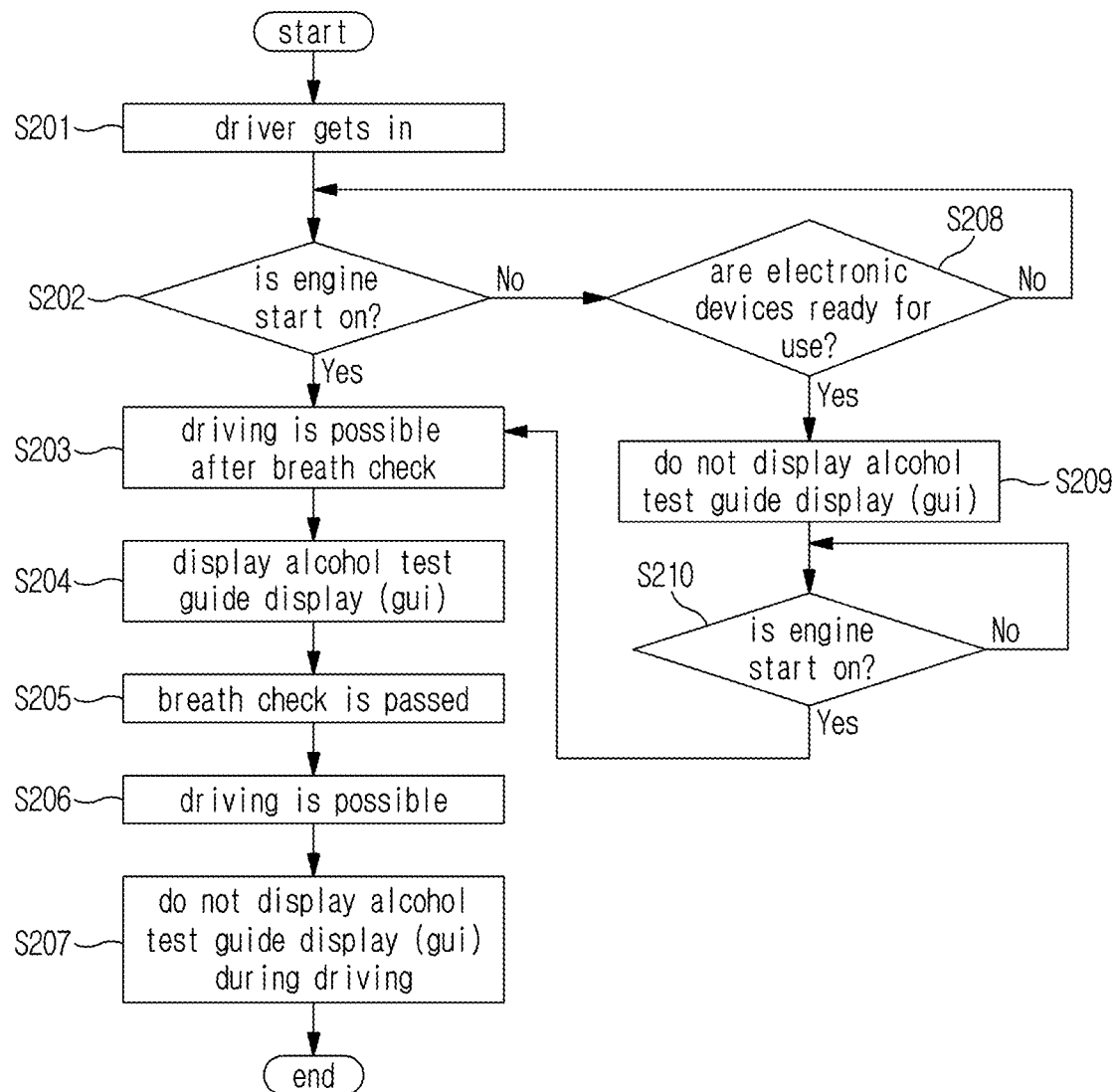
FIG. 2 is a flowchart of a display control method using a drunk driving prevention system according to the embodiment of the present disclosure.

First, FIG. 2 is a flowchart of a display control method using a drunk driving prevention system according to the embodiment of the present disclosure.

According to an embodiment of the present disclosure, the display control method using the drunk driving prevention system includes receiving an engine start input of the driver and determining whether to display the alcohol test guide information based on the engine start input of the driver.

Specifically, as illustrated in FIG. 2, when the driver gets in the vehicle (S201), which engine start input is received from the driver is checked (S202, S208). For example, as in steps S202 and S208, whether the input is the engine start-on input for starting the engine or the electronic device-on input for activating the electronic devices may be determined.

In this regard, steps S203 to S207 are executed when the engine start input of the driver is the engine start-on input, while step S209 is executed when the engine start input is the electronic device-on input switching the electronic devices into a ready-for-use state without starting the engine.

Specifically, according to the present disclosure, in determining whether or not to display the alcohol test guide information, whether or not to display the alcohol test guide information is determined according to the state of the engine start-on input by the driver. Accordingly, when the engine start input by the driver is the engine start-on input for driving the vehicle as illustrated in FIG. 2, it is determined that the driver intends to drive (drivable state after the breath-checking) and the alcohol test guide information is displayed (S203, S204). In contrast, when the engine start input of the driver is an electronic device-on input for activating the electronic devices, it may be determined that the driver does not intend to drive (electronic devices are ready for use) and the alcohol test guide information is not displayed (S209).

When an engine start-on signal is entered by the driver, the display unit displays the alcohol test guide information (S204). Then, when the drunk driving prevention system confirms that the driver is not intoxicated and the breath-checking is completed, the vehicle is switched into a drivable state (S206). On the other, while the vehicle is driving, the checking unit may not display the alcohol test guide information even if the alcohol test guide information needs displaying (S207).

On the other hand, when the electronic device-on signal is entered by the driver, the alcohol test guide information is not displayed, and whether the engine start-on signal is entered by the driver is checked again (S210). When the engine start-on signal is entered, the vehicle is switched into a drivable state after the breath-checking and the alcohol test guide information may be displayed.

On the other hand, in displaying the alcohol test guide information in step S204, other information about the vehicle such as low tire pressure, power supply check, and the like needs displaying over the alcohol test guide information in some cases.

For example, the vehicle controller may dictate the display of the vehicle state guide information relating to the internal devices while the alcohol test guide information is displayed in the breath-checking process. In this regard, according to the preferred embodiment of the present disclosure, the vehicle state guide information may be classified into safety feature information and convenience feature information, and the output of the display unit may be prioritized by way of prioritizing the safety feature information and the convenience feature information with respect to the alcohol test guide information in advance.

For example, the guide information on the drivetrain, wheels, and power-related equipment such as low tire pressure, engine system error, power supply check, brake system check, hybrid system check, and the like is directly related to vehicle safety, is thus classified into the safety feature information, and may be prioritized over the alcohol test guide information. In contrast, the guide information relating to a user input state such as a system call for gas mileage and driving distance, display of item lists to be selected by a user through the operation system, and the like is not directly related to vehicle safety, is thus classified into convenience feature information, and is subordinated to the alcohol test guide information.

Accordingly, in displaying the vehicle state guide information transmitted from the vehicle controller, the display unit stops displaying the alcohol test guide information and displays the safety feature information instead when the display of the safety feature information is requested while the alcohol test guide information is displayed. On the other hand, when the display of the convenience feature information is requested while the alcohol test guide information is displayed, the display unit may display the convenience feature information after the alcohol test guide information is terminated.

Figure 3:
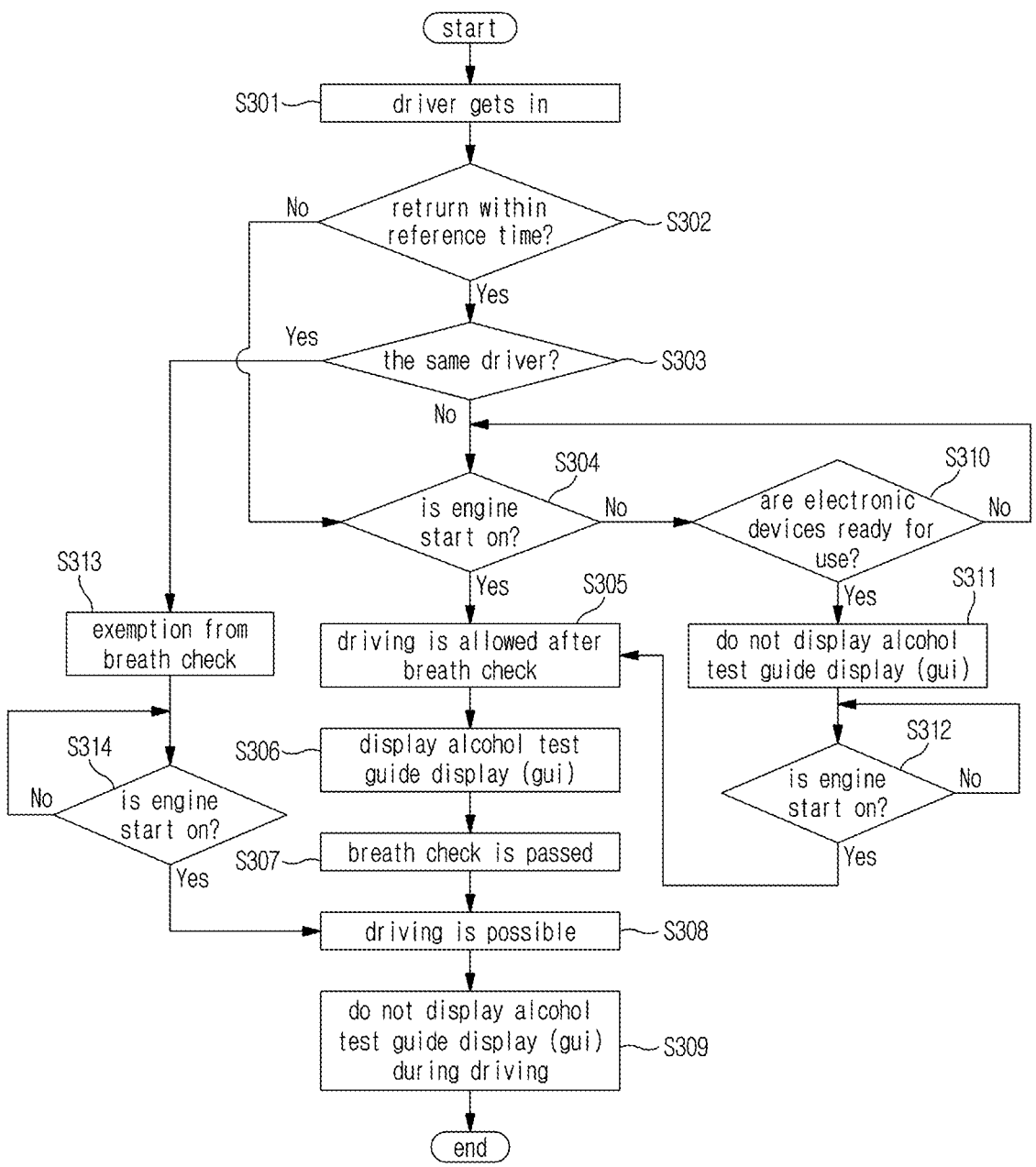
FIG. 3 is a flowchart of a display control method using a drunk driving prevention system according to another embodiment of the present disclosure.

FIG. 3 is a flowchart of a display control method using a drunk driving prevention system according to another embodiment of the present disclosure.

Unlike FIG. 2, a step of checking whether the same driver is eligible for exemption from the breath-checking is further included in FIG. 3. That is, according to the embodiment in FIG. 3, when the same driver returns to the vehicle within a reference time (for example, within a few minutes), alcohol test guide information is not displayed for a repeated breath-checking so that the driver is exempt from the breath-checking and the vehicle is immediately switched into a drivable state.

Specifically, when the driver gets in the vehicle (S301), whether the driver returns to the vehicle within the reference time after the previous driving ended (S302), and whether the driver is the same driver (S303) if the driver returns to the vehicle within the reference time are determined. The order of steps S302 and S303 may be reversed when the return of the same driver is checked.

When the same driver does not return or when the same driver returns after the reference time, the same control process following the engine start input described in FIG. 2 is repeated.

That is, when it is determined that the engine start input of the driver is the engine start-on input for driving the vehicle in step S304, it may be determined that the driver intends to drive (drivable state after the breath-checking) and the alcohol test guide information is displayed (S305, S306). In contrast, when it is determined that the engine start input of the driver is the electronic device-on input for activating the electronic devices, it may be determined that the driver does not intend to drive (the electronic devices are ready for use) and the alcohol test guide information may not be displayed (S311).

When the engine start-on signal is entered by the driver, the alcohol test guide information is displayed through the display unit (S306), Then, when the drunk driving prevention system confirms that the driver is not intoxicated and the breach check is completed, the vehicle is switched into a drivable state (S308). On the other, the checking unit may not display the alcohol test guide information even if the alcohol test guide information needs displaying while the vehicle is driving (S309).

On the other hand, when the electronic device-on signal alone is entered by the driver (S310), the alcohol test guide information is not displayed (S311) and whether the engine start-on signal is entered by the driver is checked again (S312). When the engine start-on signal is entered, the vehicle is switched into a drivable state after the breath-checking and the alcohol test guide information may be displayed.

On the other hand, the information captured by the camera may be used in determining whether the returned driver is the same in step S303. For example, the image information captured by the camera in the breath-checking process during the previous driving may be stored in the storage unit. In addition, when the driver returns to the vehicle, the camera photographs the driver seated in the driver's seat again, and the captured image is processed by the image processing unit and then compared with the image information stored in the storage unit during the previous driving so that the check unit may check whether the driver is the same.

When it is confirmed that the driver is the same in step S303, the check unit may exempt the driver from the breath-checking (S313), and the alcohol test guide information may not be displayed (S309) when the engine start-on input of the driver is entered (S314).

The drunk driving prevention system and the method of controlling the alcohol test guide information display may prevent unrequired guide information from being displayed, thereby reducing the inconvenience of the driver.

Figure 4:
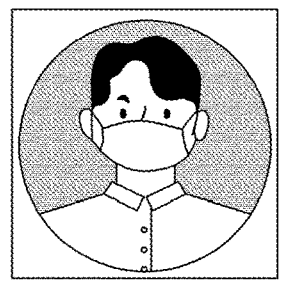
FIG. 4 is a view illustrating the wear and non-wear of a facial mask for describing a criterion for determining whether a facial mask is worn.
Figure 4:
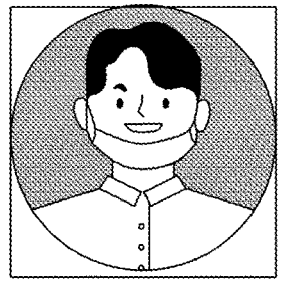

FIG. 4 is a view illustrating the wear and non-wear of a facial mask for describing a criterion for determining whether a facial mask is worn.

As illustrated in FIG. 4, whether a facial mask is worn is determined based on the image captured by the camera 300 provided in the vehicle, and whether the mouth of the photographed driver is covered by the facial mask may be determined. Accordingly, when the mouth is covered during the breath-checking as illustrated in FIG. 4A, it may be determined that a facial mask is worn, and when the mouth of the driver is not covered as illustrated in FIG. 4B, it may be determined that a facial mask is not worn.

The control module 200 may include the image processing unit 230 for processing images captured by the camera 300, and the image processing unit 230 may process the captured image data and directly provide the check unit 210 with the information that allows distinction between the wear and non-wear of a facial mask. In this case, the check unit 210 determines whether a facial mask is worn according to the information provided by the image processing unit 230 and maintains or changes the reference breath volume based on the result.

Figure 5:
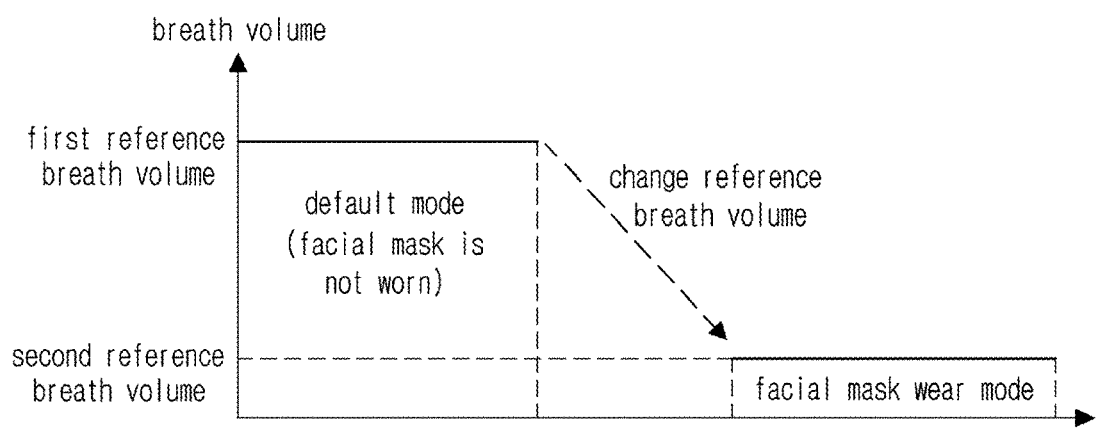
FIG. 5 is a view illustrating an example in which the drunk driving prevention method having a facial mask wear mode according to an embodiment of the present disclosure applies varying breath volume needed in a breath-checking depending on the wear or non-wear of the facial mask.

FIG. 5 illustrates an example in which the drunk driving prevention method having a facial mask wear mode according to an embodiment of the present disclosure applies varying breath volume needed for the breath-checking depending on the wear or non-wear of the facial mask.

As described above, since the volume of exhaled breath pulled into the sensor module 100 is reduced when a facial mask is worn even if the driver exhales the same level of breath, the drunk driving prevention system may not recognize the pulled breath as the normal breath of the driver when the reference breath volume set in the sensor module 100 and the control module 200 is kept at the same value.

Accordingly, in the present disclosure, when a facial mask is worn as illustrated in FIG. 5, the drunk driving prevention system resets the reference breath volume needed for breath-checking downward to facilitate the breath-checking.

Accordingly, a second reference breath volume is set to a lower value than a first reference breath volume applicable when a facial mask is not worn, and the breath-checking is performed based on the second reference breath volume when it is confirmed that the driver wears a facial mask.

Accordingly, the control module 200 is set to complete the breath-checking in a default mode only when the breath volume of the driver supplied into the sensor module 100 is equal to or greater than the preset first reference breath volume, while the reference breath volume needed for completing the breath-checking is reset downward to a second reference breath volume in the facial mask wear mode in which the driver wears a facial mask.

At this time, the reason for not setting the breath volume for breath-checking to a minimum from the beginning is that a third occupant may easily perform a vicarious breath-checking when the reference breath volume is set to the minimum equal to the second reference breath volume in the default mode and that, when the third occupant is intoxicated, the alcohol and a small amount of carbon dioxide drifting in the air may compromise the breath-checking to produce an erroneous determination result.

On the other hand, when the control module 200 resets the reference breath volume downward, the reference breath volume may be directly reset to a lower value by the check unit 210 of the control module 200, or the reference breath volume relating to the sensitivity of the sensor module 100 may be directly lowered.

For example, when the reference breath volume is reset downward by the check unit 210 of the control module 200, the check unit 210 may verify the validity of the breath volume information and the measured alcohol content transmitted from the sensor module 100 to the control module 200 while the sensitivity of the sensor module 100 is set sufficiently low. In contrast, when the reference breath volume relating to the sensitivity of the sensor module 100 is directly lowered, the sensor module 100 may measure the alcohol content in the default mode only when the breath volume of the driver pulled into the sensor module 100 is equal to or greater than the first reference breath volume, and the sensor module may measure the alcohol content in the facial mask wear mode even when the pulled breath volume is equal to or greater than the second reference breath volume and less than the first reference breath volume.

According to the embodiment of the present disclosure, the drunk driving prevention system having the facial mask wear mode may include the display unit 400 for displaying various information in the system. The display unit 400 may be a display of the vehicle cluster or may include a separate display or notice device.

In addition, according to the preferred embodiment of the present disclosure, the drunk driving prevention system may include in the display unit 400 a notice device configured to sound an alarm to relay the information relating to the operation of the drunk driving prevention system to the inside of the vehicle.

In particular, according to the preferred embodiment of the present disclosure, the drunk driving prevention system may be a system that includes the control module and the sensor module to implement a bypass mode in a narrow sense or may be a system that includes configurations such as a camera, a storage unit, a display unit, and a notice device in a broad sense. However, configurations such as a camera and a storage unit are not ruled out even in the system in a narrow sense, and the system may be implemented by interlocking a camera, a storage unit, and a display unit provided in a vehicle system with the control module and sensor module.

The display device 400 may display various information that the driver needs to be informed of in the process of operating the drunk driving prevention system. In particular, relevant information may be displayed when the drunk driving prevention system enters the facial mask wear mode.

In displaying whether the facial mask wear mode is entered, the display unit 400 may directly display the current mode (default mode or facial mask wear mode) information or only display the guide information when the facial mask wear mode is entered.

For example, the display unit 400 may output guide information for the driver to be positioned close to an inlet of an inhaling unit 110 of the sensor module 100 when the facial mask wear mode is entered.

In this case, the display unit 400 may display on the screen an instruction phrase to approach the inlet of the inhaling unit 110 of the sensor module 100 together with the image information on the position of the inlet of the inhaling unit 110.

In addition, according to the present disclosure, when it is determined that the driver wears a facial mask, the driver may be guided to a seating position such that the driver may effectively blow the exhalation into the inlet of the inhaling unit of the sensor module 100 as the facial mask wear mode is entered.

Figure 6:
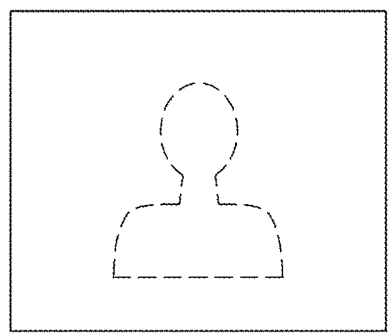
FIG. 6 is a view illustrating frames for captured mages respectively provided in each mode.
Figure 6:
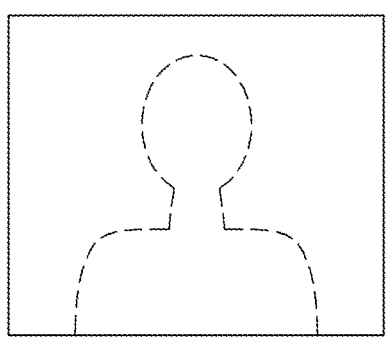

In this regard, FIG. 6 illustrates frames (dotted line) for the captured images respectively provided in the default mode and the facial mask wear mode.

As illustrated in FIG. 6A, a frame (dotted portion) for the upper body including the facial contour of the driver is provided in the default mode in consideration of the general seating position of the driver. That is, the camera 300 transmits the captured image information to the image processing unit 230 of the control module in real-time, and the image processing unit generates a frame for the facial position of the driver and processes the image so that the captured image matches the frame. The image information including the frame is transmitted to the display unit 400, and the display unit 400 may output the image information matching the frame in real-time.

In contrast, the driver may be guided to a position closer to the inlet of the inhaling port of the sensor module 100 in consideration of the reduced breath volume due to the facial mask wear in the facial mask wear mode. To this end, according to the preferred embodiment of the present disclosure, as illustrated in FIG. 6B, when the facial mask wear mode is entered, the image processing unit 230 provides the display unit 400 with a frame (dotted portion) enlarged at a preset proportion so that the driver may position himself such that the facial contour matches the enlarged frame. The camera and the inhaling port of the sensor module are preferably aligned, and the position of the enlarged frame may be properly adjusted in consideration of the position of the camera and the sensor module. The enlargement proportion and position of the frame may be stored in the control module or the storage unit in advance.

Accordingly, the driver is encouraged to be as close as possible to the inlet of the sensor module, thereby alleviating the problem of reduced breath volume when a facial mask is worn.

According to still another embodiment of the present disclosure, the sensor control unit 240 of the control module 200 may command or control the sensor module 100 to increase the rotation speed of the fan installed on the inlet side of the inhaling port so that a sufficient volume of exhaled breath of the driver may be pulled into the sensor module 100 when the facial mask wear mode is entered.

When the normality of the breath of the driver is confirmed according to the criterion in each mode through these processes, the check unit 210 completes the breath-checking.

On the other hand, when the check unit 210 completes the breath-checking, the sensor module 100 measures the alcohol content in the exhaled breath of the driver. The information of the measured alcohol content is transmitted to the control module 200, and the determination unit 220 of the control module 200 may compare the alcohol content measured by the sensor module 100 with the reference alcohol content to check the intoxication state of the driver.

When the comparison result shows that the measured alcohol content of the drives exceeds the reference alcohol content and that the driver is intoxicated, the determination unit 220 determines that the driver may not drive due to intoxication and causes the vehicle control unit 250 of the control module 200 to activate the engine start block device 630. In this regard, the engine start block device 630 refers to a device that disables the vehicle by blocking the engine start.

In addition, the control module 200 may include the storage unit 500, and the storage unit 500 may store various information such as the image information captured by the camera 300, alcohol content information measured by the sensor module 100, and the like. The stored information may be provided to the relevant institutes in the future.

In addition, the storage unit 500 may store the vehicle information including the open/closed state of windows before breath-checking and the operating state of the air conditioner. The intoxication state of the driver needs to be checked in the inside air mode with all the windows 620 closed for accurate measurement. Once the breath-checking starts, the control module 200 may close the vehicle windows 620 and switch the vehicle into the inside air mode. To this end, the vehicle control unit 250 of the control module 200 may transmit control commands to control the opening/closing of the vehicle windows 620 and the inside/side air modes of the air conditioner 610. In addition, the vehicle control unit 250 may close the vehicle doors to perform the breath-checking.

Here, the information stored before the breath-checking refers to the information on the surrounding environment set by the driver before the breath-checking, and accordingly, the control module 200 may switch the vehicle state as per the vehicle information stored in the storage unit 500 before the breath-checking to return the in-vehicle devices 600 to the previous setting after the breath-checking is completed. However, since opening the vehicle doors is impossible, the storage unit 500 preferably does not store the door state.

According to the embodiment of the present disclosure, the drunk driving prevention system may further include a biometric check unit 700 for identifying the driver. The biometric check unit 700 is for checking the information of the current driver and may include a biometric verification device configured to check the fingerprint or iris information of the driver.

The storage unit 500 may store the biometric information of a specific driver in advance, and the check unit 210 may compare the stored biometric information and the biometric information of the current driver obtained by the biometric check unit 700 to process the identification of the driver.

Regarding the identification process of the driver, when the driver who completed the breath-checking and intoxication state check returns to the vehicle within a short time, the engine start is allowed without going through the breath-checking when certain conditions (for example, short stop or short leaving from the driver's seat) are satisfied.

Figure 7:
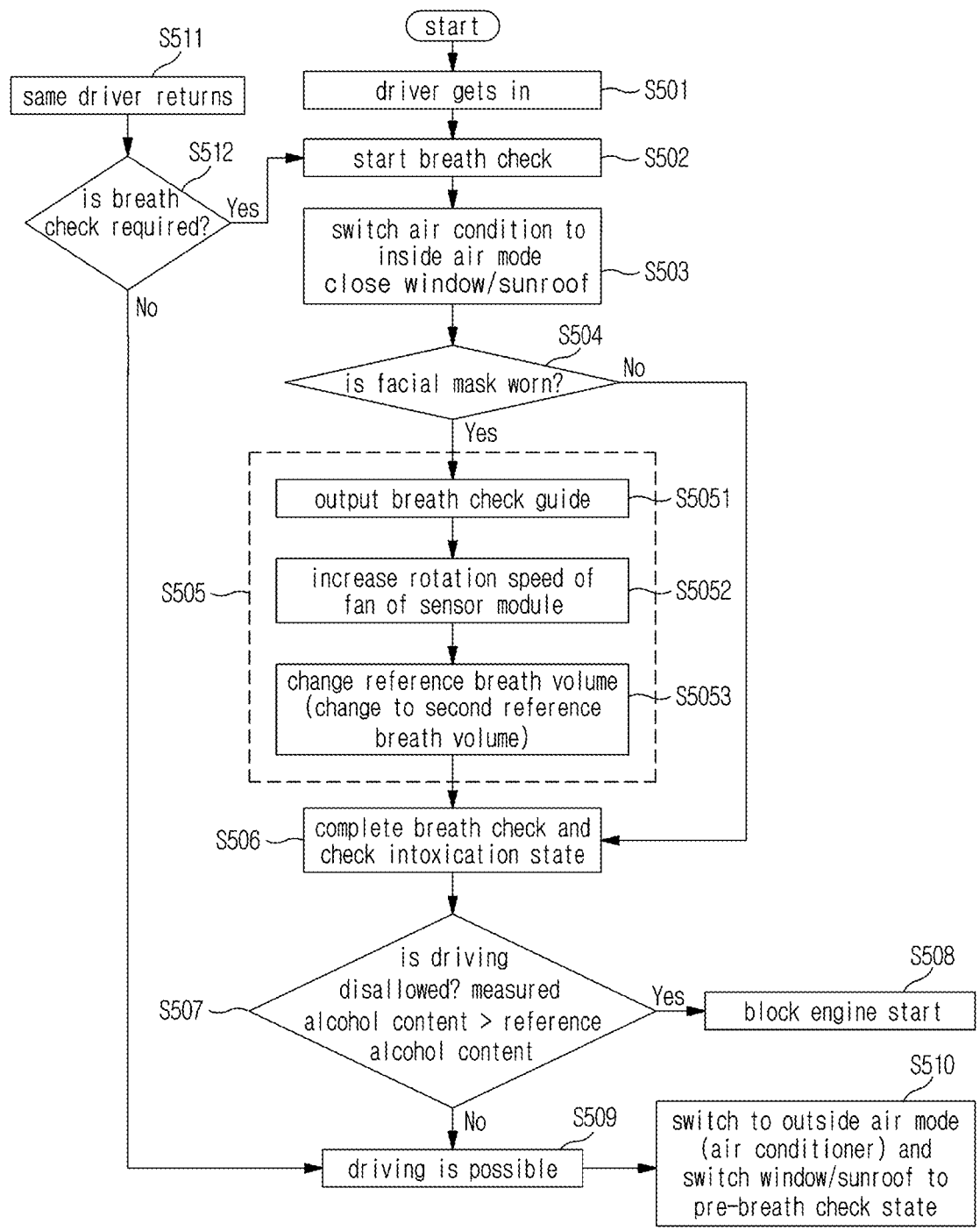
FIG. 7 is a flowchart of a drunk driving prevention method having a facial mask wear mode according to an embodiment of the present disclosure.

Specific steps of a drunk driving prevention method using the drunk driving prevention system with these configurations and the facial mask wear mode are illustrated in FIG. 7.

According to the present disclosure, the drunk driving prevention method having the facial mask wear mode includes starting a breath-checking at the request of a driver, determining whether a driver wears a facial mask based on an image captured by the camera, determining whether the driver is intoxicated by measuring the alcohol content in the exhaled breath of the driver by a control module when breath volume pulled into the sensor module is equal to or greater than a reference breath volume, and determining whether or not to block the start based on the determination result of the intoxication state of the driver. In particular, the control module may apply varying reference breath volume of the sensor module depending on the wear or non-wear of a facial mask.

As illustrated in FIG. 7, when the driver gets in the vehicle (S50), the check unit starts the breath-checking (S502). The vehicle control unit of the control module may switch the air conditioner into the inside air mode at this time and close windows (sunroof included) (S503).

The check unit may check whether the driver wears a facial mask while the vehicle is sealed (S504). The breath-checking proceeds in the default mode when it is confirmed that the driver does not wear a facial mask. Accordingly, when the breath volume pulled into the sensor module is equal to or greater than the preset first reference breath volume, the breath-checking is completed and the alcohol content in the exhaled breath of the driver and the intoxication state are checked (S506).

On the other hand, when the driver is determined to wear a facial mask in step S504, the facial mask wear mode is entered and the breath-checking starts in the default mode. Accordingly, switching into the facial mask wear mode is performed in this step (S505), and switching into the facial mask wear mode (S505) may include outputting a breath-checking guide (S5051), increasing the rotation speed of the fan of the sensor module (S5052), and changing the reference breath volume needed for the breath-checking to the second reference breath volume (S5053).

In this regard, the outputting of a breath-checking guide may be the outputting of an instruction for the driver to approach the inlet by the display unit. In addition, in the outputting of the breath-checking guide (S5051), the frame of the real-time image captured by the came and output by the display unit may be enlarged at a preset proportion to be provided.

FIG. 7 illustrates an example in which the switching into the facial mask wear mode includes all steps S5051, S5052, and S5053. However, this is just an illustrative embodiment of the present disclosure, and the switching into the facial mask wear mode may include one or more of steps S5051, S5052, and S5053.

However, it is preferable that the changing of the reference breath volume needed for the breath-checking (S503) is indispensably included to facilitate the breath-checking.

In addition, FIG. 7 illustrates a sequential execution of steps S5051, S5052, and S5053. However, this is just an illustrative example, and S5051, S5052, and S5053 may be executed in a different order.

When the facial mask wear mode is entered and the breath volume pulled into the sensor module is equal to or greater than the preset second reference breath volume, the breath-checking is completed and the determination unit of the control module checks the intoxication state based on the alcohol content in the exhaled breath of the driver measured by the sensor module (S506).

Whether the alcohol content measured by the sensor module exceeds the preset reference alcohol content is determined in checking the intoxication state (S507), and the engine start block device may block the engine start when the intoxicated driver may not drive the vehicle due to intoxication (S508). When the control module determines that the measured alcohol content of the driver exceeds the reference alcohol content and that the driver is intoxicated, it is determined that the driver may not drive the vehicle and the control module issues a blocking command that activates the engine start block device.

In contrast, when no alcohol is detected in the exhaled breath of the driver, or when the alcohol content measured by the sensor module is equal to or less than the reference alcohol content, the driving is considered allowed and the state in which the vehicle may be started is maintained (S509).

In addition, according to the preferred embodiment of the present disclosure, storing in the storage unit the image information captured by the camera and the alcohol content information measured by the sensor module before the engine start may be further included.

On the other hand, in the starting of the breath-checking (S502), the vehicle information including the open/closed state of the windows before the breath-checking and the operating state of the air conditioner may be stored in the storage unit 500.

Accordingly, the vehicle state information before the control module closes the vehicle windows and switches the vehicle into the inside air mode is stored in step S503, and the stored information may be utilized after whether or not to start the engine is determined. In this case, after whether or not to start the engine is determined, that is, after the breath-checking and alcohol test are completed and driving is allowed, the control module may switch the vehicle state as per the vehicle information stored in the storage unit before the breath-checking is completed (S510).

FIG. 7 includes the control logic for the case in which a driver returns to the vehicle within a short time after initial boarding. For example, when a driver who completed the breath-checking and the intoxication state check leaves the vehicle for a while and returns, it may be unrequired to go through the breath-checking again. Accordingly, according to the embodiment of the present disclosure, when the same driver returns (S511), whether or not a repeat breath-checking is required may be checked (S512). Whether a repeat breath-checking is required may be determined based on the comparison between the time the vehicle is stopped or the driver vacates the driver's seat and the reference value. When the reference value is exceeded, it may be determined that a repeat breath-checking is required.

In contrast, a comparison of the check information by the check unit or the biometric check device shows that the driver is the same driver as in the previous check returns and the time requirement relating to the time the vehicle is stopped or the driver vacates the driver's seat is satisfied, the vehicle may be immediately driven without a repeat breath-checking.

According to the present disclosure, when the camera 300 of the drunk driving prevention system attempts to capture images, the check unit 210 may inform the driver of the image captured by the camera 300. In this regard, when the camera 300 is activated to capture images while the breath-checking process relating to the breath-checking is under way or the vehicle is driving, the check 210 unit may command the notice device which is a part of the display unit 400 in the vehicle to provide various types of notices informing the driver in advance.

The notice provided by the notice device may take various forms recognizable to a person by sight, hearing, and smell. For example, the notice may be provided in the form of a visual notice such as lighting a state indicator provided in the camera 300 or an interior lamp or displaying a cluster, AVN, or HUD pop-up message. In addition, the notice provided by the notice device may be an audible notice such as a specific sound, or an olfactory notice such as spraying an air freshener. In addition, the notice may take a form of a tactile notice such as a seat vibration felt by the driver. In addition, the notice by the alarm device is not limited to one form of notice classified as a visual, audible, smell, or tactile notice. The notice may change from one form to another as per the driver setting, or the driver may set such that two or more notices may be simultaneously provided.

On the other hand, the notices may be compared according to the levels recognized by the occupants, and the present disclosure describes the levels in terms of 'recognition intensity'. The 'recognition intensity' may be used as a measure of determining the level to which a specific notice is recognized by a person. In this regard, the 'recognition intensity' may be a numerical value calculated according to a quantified value for each notice type and does not refer to the numerical concept expanded to encompass different types for comparison but may refer to the intensity by which different types of notices may be compared for superiority. For example, in the case of audible notice, the loudness of the sound may be the 'recognition intensity. For example, the sound having a higher decibel may be treated as a notice having greater 'recognition intensity'. Accordingly, according to the present disclosure, having a 'higher recognition intensity' may mean having a greater intensity among the same type of notices. On the other hand, the rank of 'recognition intensity' may be determined even when different types of notices are included, and in this case, a notice having a higher 'recognition intensity' may include all types of notices having lower 'recognition intensity'. However, even in this case, when it comes to the intensity comparison of the type having a relatively low 'recognition intensity', a notice having a high recognition intensity preferably has a higher intensity with respect to the same type of notice.

Regarding the 'recognition intensity', according to the preferred embodiment of the present disclosure, the 'recognition intensity' of the notice provided according to a situation may be set differently according to the importance.

In addition, according to the preferred embodiment of the present disclosure, the breath-checking processes before and during driving are distinguished. While the vehicle is driving, the image capture notice is already issued as the immediately previous breath-checking is completed so that outputting the image capture notice is less important while the vehicle is driving than while the breath-checking process is under way. Therefore, according to the preferred embodiment of the present disclosure, whether the image capture notice is indispensable may depend on whether the breath-checking of the driver is under way or the vehicle is driving. In this regard, according to the preferred embodiment of the present disclosure, the image capture notice is indispensable when the breath-checking process is under way, while the image capture notice is elective while the vehicle is driving. Provision of the image capture notice in the breath-checking process may be set differently depending on whether an advance notice is issued.

In this regard, basically, it is preferable to inform the driver before the image capture starts so that the driver may recognize the start of the image capture. However, according to the preferred embodiment of the present disclosure, the driver setting may specify whether the advance image capture notice is required in the check unit. In this case, the check unit may check the setting to determine in advance whether the image capture notice is required and determine whether or not to provide the notice each time an image is captured or to omit the notice when an image is captured.

For example, the drunk driving prevention system may provide a setting menu regarding whether or not to provide image capture notice and the driver may select to omit the image capture notice by setting. In such a setting, the drunk driving prevention system may omit image capture notice while the system is operating.

On the other hand, according to an embodiment of the present disclosure, the system may be configured such that the driver is informed in advance of the image capture in the breath-checking process before the breath-checking starts when the vehicle is first started. When the driver is informed of the image capture before the breath-checking starts, it is considered equivalent to an advance image capture notice so that the image capture notice may be treated as unrequired. In this example, the image capture by the camera may be announced in advance by outputting on the display unit a message that an image will be captured by the camera or providing an audio message to the same effect before the breath-checking starts. Accordingly, the image capture notice by the check unit may be set such that the image capture notice is omitted at the time of image capture by the camera.

In addition, according to the present disclosure, the image capture notice is preferably provided for each image capture unless the driver selects notice omission in advance.

However, when the driver who completed the immediately previous breath-checking returns to the driver's seat, the driver is deemed to have received the notice so that the image capture notice may be omitted.

On the other hand, according to another embodiment of the present disclosure, even when the same driver returns, whether the driver returns within a certain time after the driver gets leaves the vehicle may determine whether a repeat breath-checking is required. At this time, when the repeat breath-checking is unrequired, that is, when the driver returns within the reference time (for example, within a few minutes), the image capture notice may be omitted and the image information captured by the camera may be stored without a notice.

In contrast, when the driver returns after the reference time, a repeat breath-checking is considered required and the driver may be given the image capture notice as per the image capture notice setting as in the usual breath-checking process.

In addition, even when the normal breath-checking is completed and the vehicle is driving, the image capture notice may be selectively provided as per the image capture notice setting. In this case, when the driver setting specifies that no image capture notice is required, the image capture notice may be omitted when an image is captured by the camera.

On the other hand, another feature of the preferred embodiment of the present disclosure is that whether an image capture attempt is normal or abnormal is determined and different image capture notices may be provided depending on the determination result.

In this regard, according to the preferred embodiment of the present disclosure, when the vehicle is stopped, that is, when the breath-checking of the driver is unrequired because the vehicle is stopped, an image capture attempt may be regarded as unlawful and the occupants may be provided with an image capture notice. The image capture notice under such a circumstance may be provided in a form different from the notice form of the image capture attempt under normal breath-checking situation. For example, the occupants may preferably be provided with a notice of high level, that is, a notice of relatively higher recognition intensity, so that the occupants may recognize the camera action immediately. Accordingly, an image capture notice (second alarm) having a stronger recognition intensity than the image capture notice (first alarm) in the normal image capture attempt as in the breath-checking process may be provided. For example, when both the first and second alarms are provided as a sound, the second alarm may be a rapidly repeating warning sound at a louder volume.

Once it is determined that an image capture approach by a camera is made in an abnormal route and the second alarm is provided, the check unit may provide a message through the display unit for the driver to choose to agree or disagree to subsequent image capture by the camera. At this time, when the driver disagrees, the camera may be switched off immediately. However, even when the driver disagrees, whether the camera is operated normally may be checked through a system rebooting, instead of switching off the camera immediately. However, when the driver agrees, the camera is not switched off and the captured image data may be stored in the storage unit.

In this regard, specific examples of selectively providing an image capture notice through the check unit are described with reference to FIGS. 2 and 3.

On the other hand, according to the present disclosure, the drunk driving prevention system may include the image processing unit 230, the sensor control unit 240, and a vehicle control unit 250.

The image processing unit 230 receives and processes the image information captured by the camera 300 into the image information the control module 200 needs. The sensor control unit 240 is for controlling the sensor module and may control the rotation speed of the fan of the sensor module 100, the sensitivity of the sensor module 100, and the like. The vehicle control unit 250 may transmit to other in-vehicle devices 600 control commands on vehicle doors, windows/sunroof 620, an air conditioner 610, an engine start block device 630, and the like.

A specific example of a method of providing an image capture notice of the drunk driving prevention system is illustrated in FIGS. 2 and 3.

First, FIG. 2 is a flowchart of a display control method using a drunk driving prevention system according to the embodiment of the present disclosure.

According to the preferred embodiment of the present disclosure, a method of controlling an image capture notice of the drunk driving prevention system includes starting a breath-checking, providing a first image capture notice by a notice device before image capture by the camera, and capturing an image by the camera to determine, by the control module, whether the breath-checking is complete based on the images captured by the camera and the alcohol content measured by the sensor module.

Figure 8:
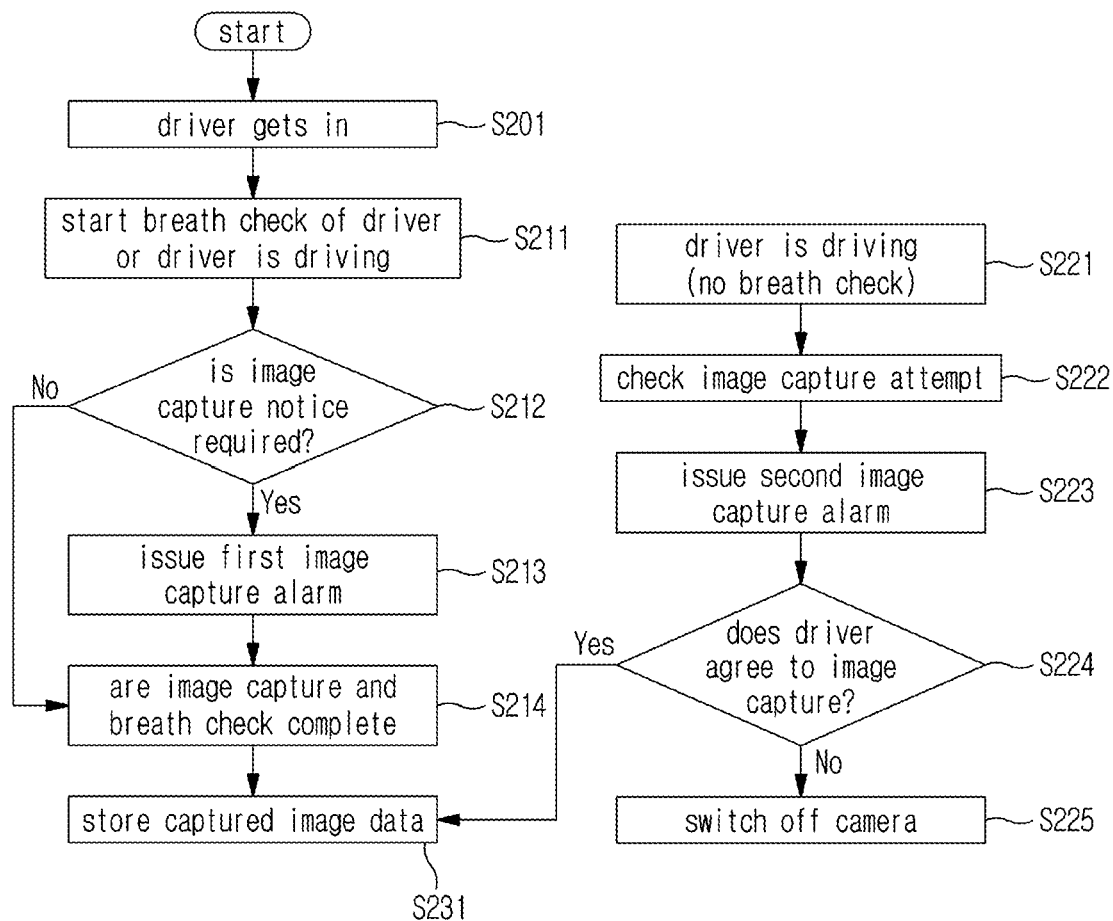
FIG. 8 is a flowchart of an image capture notice method using a drunk driving prevention system according to an embodiment of the present disclosure.

Specifically, as illustrated in FIG. 8, when the driver gets in the vehicle (S201), whether the breach check of the driver has started or the vehicle is driving (S211), and whether an image capture notice is required (S212) may be checked. When an advance image capture notice is issued or the driver setting specifies that no image capture notice is required, image capture by the camera and the breath-checking are immediately performed, and if the breath-checking is complete (S214), the capture image data is stored in the storage unit (S231). In contrast, if the image capture notice is required as usual, the notice device issues the first image capture notice (first alarm) (S213), and the capture image data is stored in the storage unit (S231) after image capture by the camera and the breath-checking are completed (S214).

On the other hand, when the breath-checking is not performed while the vehicle is stopped and the driver is in the stopped vehicle (S221) and an image capture attempt by the camera is confirmed (S222), the check unit determines that the image capture is attempted through an abnormal route and issues a second image capture notice (second alarm) (S223). At this time, it is important the image capture notice allows the driver to immediately recognize it and respond so that the second image capture notice has preferably a higher recognition intensity than the first image capture notice.

Whether the driver agrees to be photographed is checked (S224) after the second image capture notice is issued. When the driver agrees to be photographed, storage of the captured image data is allowed (S231). In contrast, when the driver does not agree to be photographed, the captured image is not stored and the camera is switched off (S225). However, when the camera is switched off and the vehicle while the breath-checking remains incomplete due to the switching-off of the camera, the display unit preferably issues a message that the driver is responsible for the drunk driving. In addition, the photographing function of the camera may be temporarily deactivated in the setting mode instead of switching off the camera in step S225. Another example is that the system may be rebooted or a message encouraging the user to visit a nearby service center may be issued instead of switching off the camera in step S225.

Figure 9:
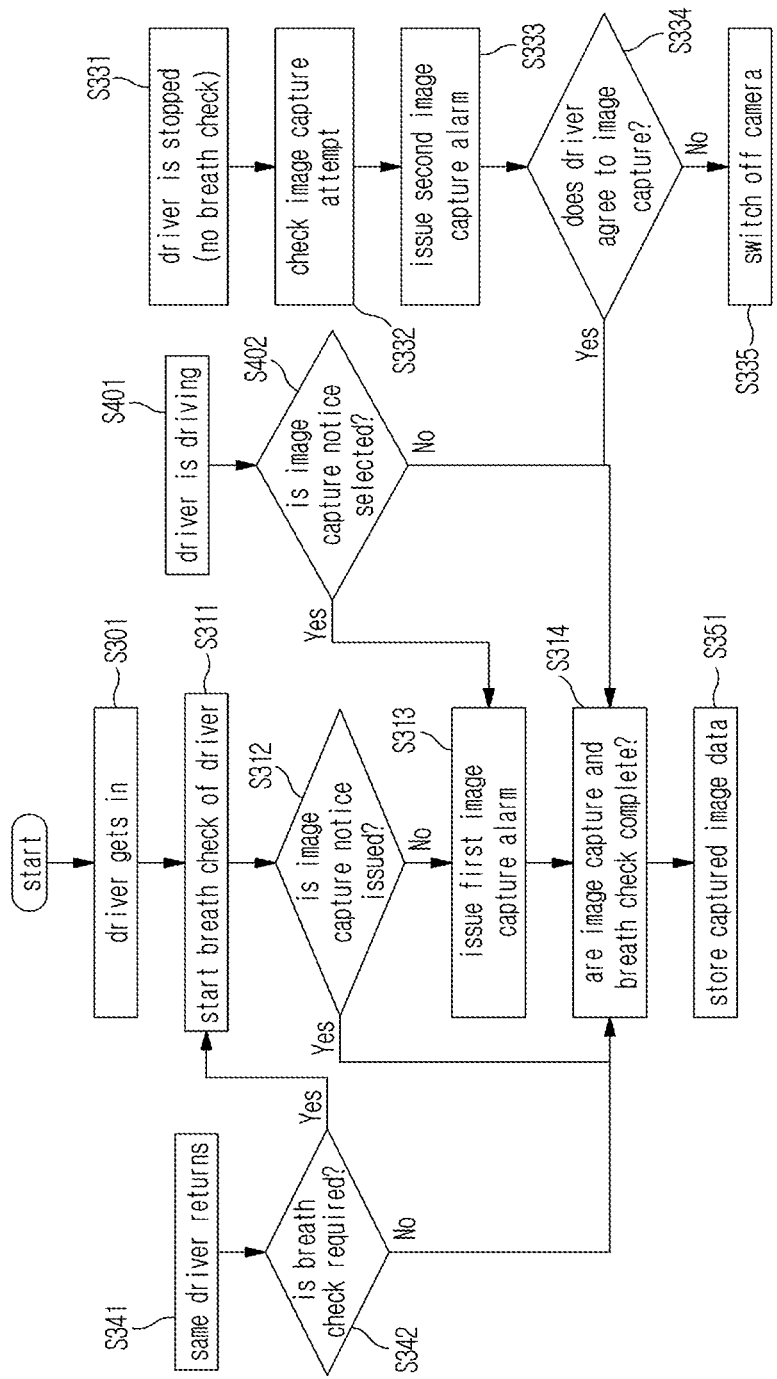
FIG. 9 is a flowchart of an image capture notice method using a drunk driving prevention system according to another embodiment of the present disclosure.

FIG. 9 is a flowchart of an image capture notice method using a drunk driving prevention system according to another embodiment of the present disclosure.

In FIG. 9, the steps in FIG. 8 are respectively separated by the initial events and described in more detail. Specifically, the flowchart in FIG. 9 describes four types of the initial state after the driver gets in the vehicle: (i) the driver gets in and breath-checking starts, (ii) the vehicle is driving, (iii) the vehicle is stopped, and (iv) the same driver returns.

First, (i) when the start of the breach check of the driver is confirmed (S311), whether an advance image capture notice is issued is checked (S312). When no advance image capture notice is issued, the notice device issues the first image capture notice (first alarm) (S313), and the captured image data is stored in the storage unit (S351) after image capture by the camera and the breath-checking are completed (S314). In contrast, when an advance image capture notice is issued, the image capture by the camera and the breath-checking are performed immediately. The captured image data is stored in the storage unit (S351) if the breath-checking is completed (S314).

(ii) While the vehicle is driving (S312), whether the driver setting specifies that the image capture notice is required is checked (S322). Steps S313 and beyond are executed when the notice is required, and image capture (S314) and the storing of the captured image data (S351) are immediately performed when the notice is not required.

(iii) When the vehicle is stopped (S331), if an image capture attempt by the camera is confirmed (S332), the check unit determines that the image capture is attempted through an abnormal route and transmits the second image capture notice (second alarm) (S333). At this time, the second image capture notice is preferably set to have a higher recognition intensity than the first image capture notice.

After the second image capture notice is issued, whether the driver agrees to be photographed is checked (S334), and the storage of the captured image data is allowed when the driver agrees to be photographed (S351). In contrast, when the driver does not agree to be photographed, the captured image is not stored and the camera is switched off (S335). Replacing the switch-off of the camera is already described in the examples in FIG. 8.

(iv) When the same driver returns, determining whether the driver is the same for the exemption from the breath-checking and omission of the image capture notice is further included. In this regard, the image information captured by the camera may be used in determining whether the driver is the same. For example, the image information captured by the came during the immediately previous breath-checking may be stored. In addition, when the driver returns, the camera may photograph the driver in the driver's seat, and the captured image may be processed by the image processing unit and compared with the image information stored in the storage unit during the immediately previous breath-checking to check whether the driver is the same.

In particular, according to the embodiment of FIG. 9, when the same driver returns within a reference time (for example, within a few minutes), photographing and storing of the photographed data are possible without going through the repeat breath-checking process. Return of the same driver within the reference time means that the image capture notice is already received so that the notice may be safely omitted.

Accordingly, when the control module determines that the driver during the immediately previous breath-checking returns to the vehicle (S341), whether the breath-checking is required is determined depending on whether the time of return is within the reference time after the time of exit (S342). When it is determined that the time of return is within the reference time and no breath-checking is required, the check unit exempts the driver from the breath-checking and immediately starts photographing. (S314). In contrast, when the time of return is past the reference time, a repeat breath-checking is considered required and the breath-checking in steps S311 and beyond is sequentially performed. At this time, the display unit may display a guide message relating to the start of the breath-checking.

Figure 10:
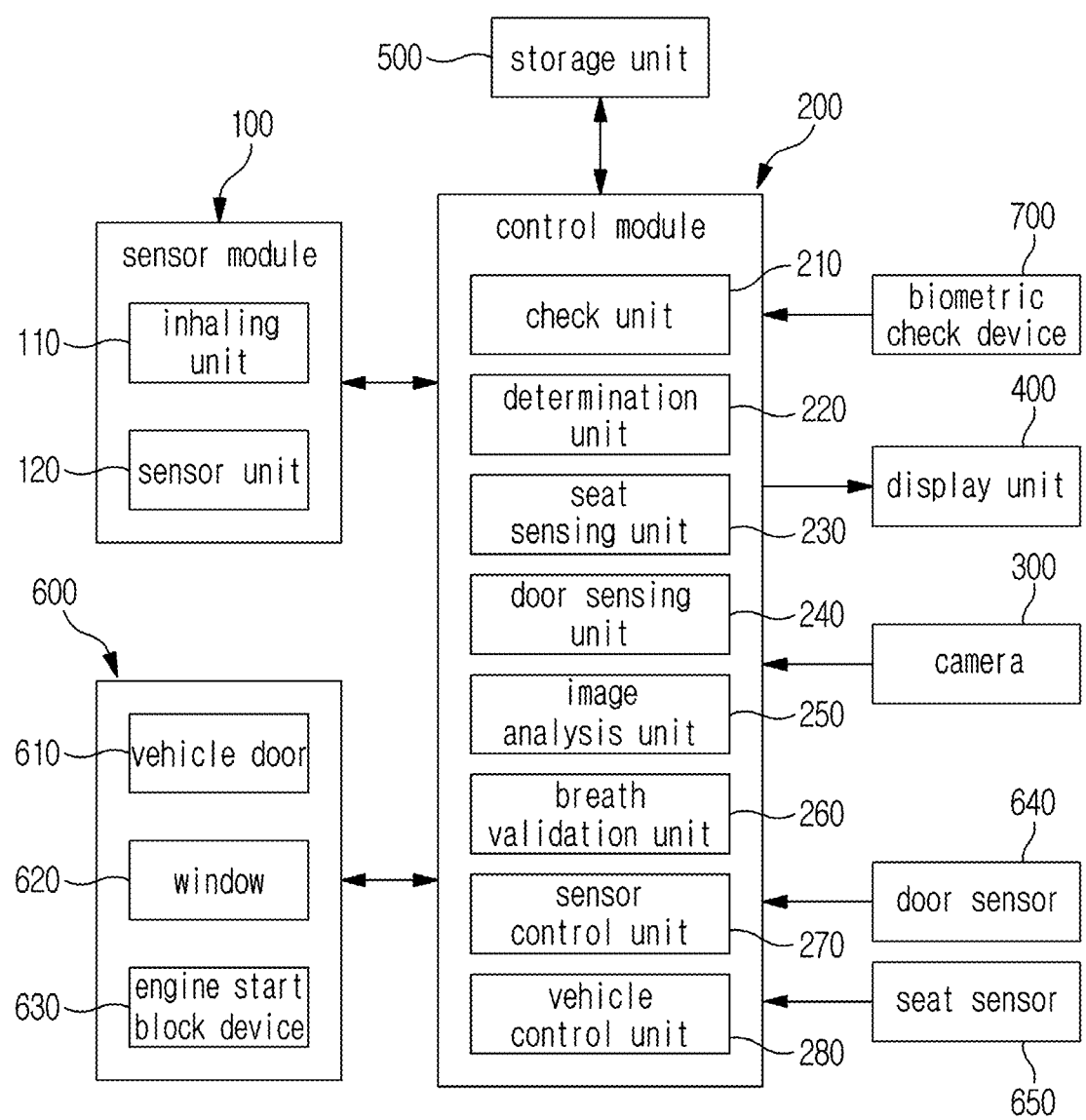
FIG. 10 is a block diagram of a drunk driving prevention system having an enhanced breath-checking process according to an embodiment of the present disclosure.

FIG. 10 is a block diagram of a drunk driving prevention system having an enhanced breath-checking process according to an embodiment of the present disclosure.

In this case, the control module 200 may be connected by the communication interface to other configurations in the system such as the sensor module 100, the camera 300, the display unit 400, and the storage unit 500, and the overall system may be controlled by the information transmitted from these configurations.

The control module 200 may include the check unit 210, the determination unit 220, a seat sensing unit 261, a door sensing unit 262, the image processing unit 263, a breath validation unit 264, the sensor control unit 240, and the vehicle control unit 250. The respective configurations included in the control module 200 are classified by the functions played by the control module 200. The respective configurations constituting the control module 200 are not necessarily meant to be physically separate. And the respective configurations of the control module may communicate with each other.

Among the respective configurations of the control module 200 illustrated in FIG. 10, the check unit 210 oversees the breath-checking process for the driver, the process being a prerequisite in determining whether the driver is intoxicated.

Basically, the check unit 210 may check whether the driver is seated from the information provided by the devices such as a weight sensor in the driver's seat or the camera 300 photographing the driver's seat.

In addition, the check unit 210 may synthesize the information provided by other configurations in the control module such as the seat sensing unit 261, the image analysis unit, the breath validation unit 264, and the like, and check whether the requirements for the completion of the breath-checking are met.

Here, the breath-checking refers to a process in which the breath of the driver is checked to check the intoxication state as the breath is pulled into the inhaling port of the sensor module. In addition, that the breath-checking is complete means that the breath of the driver is pulled into the sensor module 100, the pulled breath is checked, and the driver is determined to be fit for driving. According to the preferred embodiment of the present disclosure, the suitability of the driver's breath may be determined based on the validity of the breath. For example, whether the period of the driver's breathing pulled into the sensor module 100 matches the breathing period distinguishable by the captured image may be a criterion for determining the validity of the breath.

On the other hand, in another example, whether a movement that may be regarded as an inappropriate alcohol test attempt such as the presence of an unauthorized object in the image or a position change of a passenger may be a criterion for determining the validity of the breath of the driver.

In addition, according to the preferred embodiment of the present disclosure, that the breath-checking is complete may only mean that the volume of the driver's breath is suitable for checking the intoxication of the driver. However, unlike such an embodiment, that the breath-checking is complete may encompass the notion that the alcohol content in the checked breath is equal to or less than the reference alcohol content to be at a normal level. In this case, even if the validity of the driver's breath is recognized, the breath-checking is determined to be incomplete when the measured alcohol content exceeds the reference alcohol content.

As described above, according to the present disclosure, the check unit 210 oversees the breath-checking process. The check unit 210 checks whether the driver gets in the vehicle from the image captured by the camera 300 to start the breath-checking process and finally determines whether the breath-checking is normally completed by the respective configurations in the control module.

On the other hand, the determination unit 220 compares the alcohol content measured by the sensor module 100 with the reference alcohol content to check the intoxication state of the driver.

The determination unit may obtain the information on the alcohol content in the exhaled breath of the driver and measured by the sensor module 100 and compare the measured alcohol content with the reference alcohol content to check the intoxication state of the driver.

When the comparison result shows that the measured alcohol content of the driver exceeds the reference alcohol content, the determination unit 220 determines that the driver may not drive due to intoxication, and the vehicle control unit 250 of the control module 200 may activate the engine start block device 630. In this regard, the engine start block device 630 refers to a device that disables the vehicle by blocking the engine start and may be a device that cuts off the engine start power. On the other hand, when it is verified that the measured alcohol content of the driver does not exceed the reference alcohol content or the driver is free of alcohol, the determination unit 220 may determine that the driver may drive and allow the engine start following the engine start-on input of the driver.

Among the control module configurations in FIG. 10, the seat sensing unit 216 and the door sensing unit 262 check the information obtained from the in-vehicle sensors, in particular, a seat sensor 650 and a door sensor 640.

The seat sensing unit 261 may check the seated state of the driver and passenger and the position change of the occupants from the sensors configured to determine the presence of the occupants in the front and rear seats (driver's seat, passenger seat, and rear seat) of the vehicle. Usually, the vehicle seat sensor 650 may include a weight sensor or a capacitive sensor, and the presence and position change of the occupants may be checked from the sensed values of these seat sensors. In addition, the seat sensing unit 261 may receive information on the exit of the driver from the vehicle.

When the position change of the occupants is detected by the seat sensing unit 216 or unfastening of the seat belt by at least one occupant is detected, the check unit of the control module may determine that the detection indicates a breath-checking by an abnormal route and determine that the breath-checking is incomplete.

The door sensing unit 262 may detect the opening/closing of all doors from the open/closed states of the doors detected by the door sensors detecting opening/closing of the vehicle doors 610. In this regard, the door sensor in the present disclosure refers to a sensor configured to check the opening/closing of the windows as well as the vehicle doors, and accordingly, the door sensing unit 262 may check the opening/closing of the respective doors as well as the opening/closing of all the vehicle doors 610. When the open state of a door or window is confirmed, the vehicle control unit may transmit a control command to close the open door or a window. In this case, as illustrated in FIG. 10, the vehicle control unit may directly close the door 610 or window before the breath-checking starts. In contrast, the vehicle control unit may transmit a door/window closing message through the display unit instead of directly transmitting the control command.

The image analysis unit 263 receives and processes the image information captured by the camera 300 into the image information that the control module 200 needs or analyzes the captured image information to provide the information that the control module needs. In particular, of the image information captured by the camera, the image analysis unit may trace the changes in the mouth of the driver and calculate a first estimated breathing period by pinpointing the opening and closing time of the mouth of the driver.

In addition, the image analysis unit checks the presence of an unauthorized object other than the driver in the captured image, and the control module may not complete the breath-checking when the presence of the unauthorized object is detected.

The breath validation unit 264 checks whether the breath in the captured image matches the breath pulled into the sensor module based on the comparison result between the first estimated breathing period calculated by the image analysis unit and a second estimated breathing period determined by the change in the breath volume pulled into the sensor module. The breath validation unit 264 compares the period profile in the captured image with the period profile of the air pulled into the sensor module and checks the match between the two. Accordingly, attempts to bypass the system and pass the breath-checking by cheating such as blowing in somebody else's breath with a balloon or having a third person breathe into the sensor module.

The sensor control unit 240 may control the rotation speed of the fan in the sensor module 100, the sensitivity of the sensor module 100, and the like, and the vehicle control unit 250 transmits control commands to other in-vehicle devices 600 such as the vehicle door 610, window, engine start block device 630, and the like.

According to the preferred embodiment of the present disclosure, the control module 200 is a controller configured to perform various functions such as breath-checking, determination of intoxication, and vehicle control and may include a processor executing calculations to perform these functions and a memory storing an algorithm to execute the functions of the processor. In addition, the control module 200 may be modularly provided with the check unit 210, the determination unit 220, the seat sensor unit 261, the door sensor unit 262, the image analysis unit 263, the breath validation unit 264, the sensor control unit 240, and the vehicle control unit 250. In addition, the sub-configurations of the control module 200 are illustrative examples. The control module 200 may perform the same or equivalent functions while communicating with other vehicle controllers, in which case some sub-configurations of the control module may be removed or replaced.

In addition, according to the preferred embodiment of the present disclosure, the drunk driving prevention system having an enhanced check method may be a system that includes a control module and a sensor module to implement an enhanced check method in a narrow sense or a system that includes configurations such as a camera, a storage unit, and a display device in a broad sense. However, configurations such as a camera and a storage unit are not ruled out even in the system in a narrow sense and the system may be implemented by interlocking a camera, a storage unit, and a display unit provided in a vehicle system with the control module and sensor module.

An example of the drunk driving prevention method using the drunk driving prevention system having the enhanced check method according to an embodiment of the present disclosure may be described with reference to FIG. 11.

Figure 11:
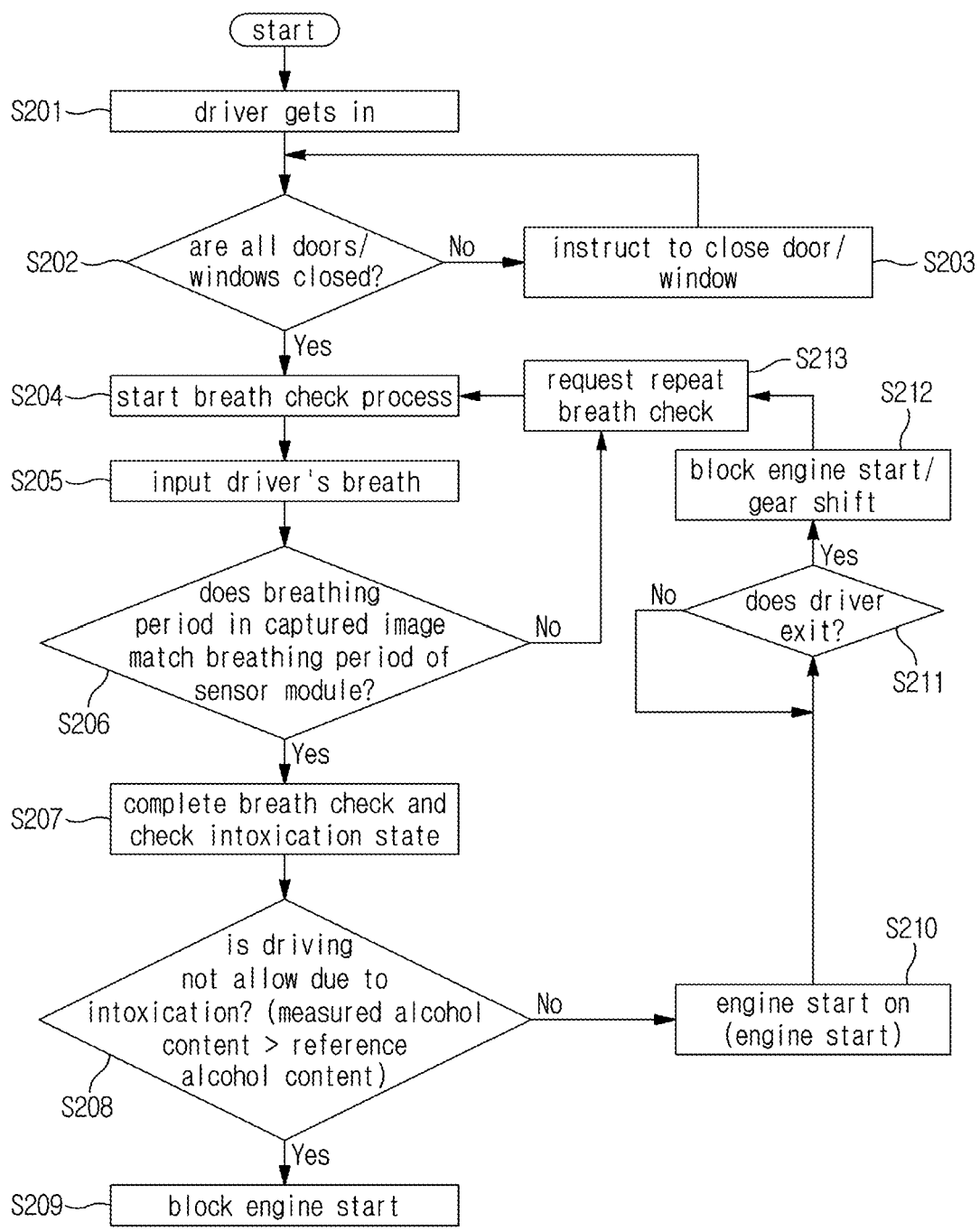
FIG. 11 is a flowchart of a drunk driving prevention method having an enhanced breath-checking process according to an embodiment of the present disclosure.

As illustrated in FIG. 11, the check unit may start with the breath-checking (S704) when the driver gets in the vehicle (S710).

At this time, the control module may check whether all the doors and windows of the vehicle are closed before the breath-checking starts (S702). At this time, whether all the doors and windows of the vehicle are closed is checked to maintain a sufficiently sealed state of the vehicle during the breath-checking. Accordingly, the control module may provide an instruction to close the open doors/windows through the display unit (S703). On the other hand, when an in-vehicle device is available to close the doors or windows, the vehicle control unit of the control module may directly close the doors and windows instead of providing the instruction to close.

The breath-checking starts with all the doors and windows closed (S704).

Once the breath-checking starts, the sensor module pulls the breath exhaled by the driver and the step of receiving the driver's breath is executed (S705).

Then, the breath validation step of checking whether the breathing period in the captured image matches the breathing period of the sensor module from the input breath of the driver (S706) is executed.

The breath validation step is executed by the breath validation unit 264 in FIG. 10 and is a step of checking and determining whether the driver's breath information measured by the sensor module substantially matches the breath exhaled by the actual driver.

Figure 12:
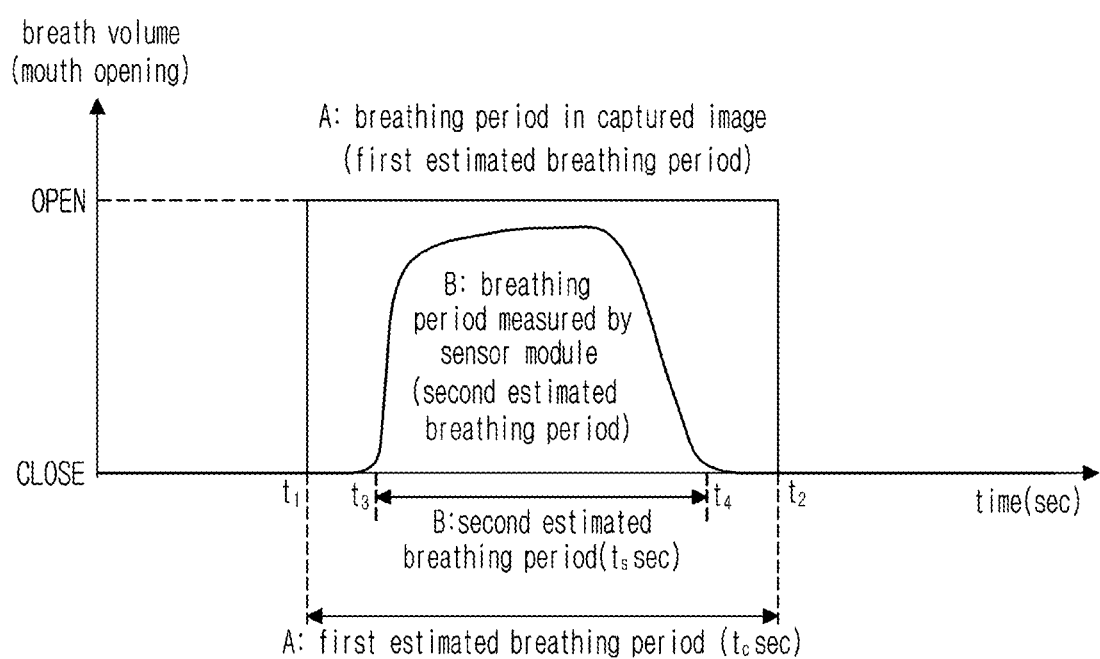
FIG. 12 is a graph describing an example of checking breath effectiveness based on a comparison between the breath volume measured by the sensor module and a mouth shape in an image.

In this regard, FIG. 12 describes a specific determination method in the breath validation step. FIG. 12 illustrates a graph describing an example of verifying the breath validity by comparing the breath volume information measured by the sensor module with the shape of the mouth in the image.

FIG. 12A represents the first estimated breathing period derived by analyzing the captured image and FIG. 12B represents the second estimated breathing period derived from the breath volume information measured by the sensor module.

Considering the time of breach check of the driver, the driver opens the mouth (OPEN) and starts to exhale during normal breathing. In addition, the driver closes the mouth (CLOSED) in the process of ending breathing, so that the start and end points of breathing by the driver may be determined from the change in the shape of the mouth of the driver in the image captured by the camera. After all, the first estimated breathing period which is the breathing period in the image captured by the camera refers to a breathing period made of the breathing start point and breathing end point of the driver estimated by the camera image. The first estimated breathing period A is the period between the start point t1 and the end point t2 obtained by the image analysis unit from the captured image, the start point t1 being the time the mouth opens in the captured image and the end point t2 being the time the mouth closes in the captured image.

On the other hand, FIG. 12B represents the second estimated breathing period which refers to a breathing period determined from the breath volume measured by the sensor module. Graph B is determined by the graph of the breath volume measured by the sensor module, the breathing period between the start point t3 and end point t4 during which breathing air is pulled into the sensor module while the breathing volume rapidly changes is set as the second estimated breathing period.

The method of verifying the breath validity using the first estimated breathing period A and the second estimated breathing period B as determined in FIG. 2 may be illustrated in the following two ways.

The first method includes comparing the total time of each period and determining that the breathing of the two periods substantially matches when the ratio of the total time tc of the first estimated breathing period with respect to the total time ts of the second estimated breathing period is within a predetermined range.

It is assumed in calculating the ratio between the two that the actual breathing takes place with the mount open. Accordingly, the second estimated breathing period with respect to the breath volume into the sensor module cannot be longer than the first estimated breathing period. In contrast, there is an invalid period in which breath is not just exhaled with the mouth open, such as the period in which exhalation is followed by inhalation with the mouth open or no breathing takes place with the mouth open, so that a margin ratio that considers such an invalid period is applied. The margin ratio may be set to 5% to 50% and may preferably be set to 5% to 20%. Too high a margin ratio may compromise the reliability of the breath validation while a low margin ratio of 5% or less may warrant an additional check which is unrequired otherwise. The margin ratio is preferably set appropriately in consideration of the accuracy of the sensor module and the image analysis accuracy of the image analysis unit.

For example, according to a preferred embodiment of the present disclosure, when the total time tc of the first estimated breathing period is equal to or greater than 100% and less than 105% (5% margin) of the total time ts of the second estimated breathing period, it may be determined that the breath in the captured image matches the breath pull into the sensor module. In addition, according to another embodiment of the present disclosure, when the total time tc of the first estimated breathing period is equal to or greater than 100% and less than 120% (20% margin) of the second estimated breathing period, it may be determined that the breath in the captured image matches the breath pulled into the sensor module.

On the other hand, the other method of verifying the breath validity may be checking whether the difference in the start time and the difference in the end time in the respective periods are less than a reference value.

In this case, the second estimated breathing period is to be included in the first estimated breathing period, and it may be determined that the breath in the captured image matches the breath pulled into the sensor module when the difference between the start time t3 of the second estimated breathing period and the start time t1 of the first estimated breathing period is less than a reference value and the end time t2 of the first estimated breathing period and the end time t4 of the second estimated breathing period is less than a reference value. Here the reference value may be set to 0.5 seconds, 1 second, etc., and this method is substantially based on the same breath validation principle as the first method.

When the breathing periods do not match in the breath validation step (S706), the breath-checking is considered invalid, and the step of requesting a repeat breath-checking without completing the breath-checking (S713) may be executed. In the step of requesting a repeat breath-checking, a request message for a repeat breath-checking may be transmitted through the display unit, or the request message for a repeat breath-checking may be issued by voice.

In contrast, when it is determined that the breathing periods match in the breath validation step (S706), the breath-checking is completed by the check unit of the control module, and the step of checking the intoxication state is executed by the determination unit (S707). According to a preferred embodiment of the present disclosure, the image information captured by the camera and the alcohol content information measured by the sensor module before the vehicle is started may be stored in the storage unit when the breath-checking is complete. The image information and the alcohol content information stored in the storage unit are the information recorded at the moment of breath-checking and may be used to present specific check information when an accident occurs later.

Whether the alcohol content measured by the sensor module exceeds the preset reference alcohol content is determined at the time of checking the intoxication state (S708), and when the intoxicated driver may not drive the vehicle, the engine start block device may be activated to block the engine start (S709). When the control module determines that the measured alcohol content of the driver exceeds the reference alcohol content in this step, it is determined that the driver may not drive due to intoxication, and the control module may transmit a control command to activate the engine start block device.

When no alcohol is detected in the exhaled breath of the driver or the alcohol content measured by the sensor module is equal to or less than the reference alcohol content, driving is considered allowed and the engine is started by turning on a starter (S710).

On the other hand, while the engine is running after the breath-checking is completed by the control module, sometimes the validated driver leaves the vehicle and another driver gets in instead and deceptively bypasses the breath-checking process. According to a preferred embodiment of the present disclosure, to prevent such a deceptive breath-checking, the exit of the driver is detected (S711), and when it is determined that the driver exits the vehicle after the vehicle is started, the step of blocking engine start and gear shift may be executed (S712). The vehicle control unit may transmit a control command to another controller to control the engine and transmission such that the engine start and gear shift may be blocked Since the driver is allowed to resume driving only after completing the repeat breath-checking when the engine start and gear shift are blocked, the system may inform the driver that the driver is required to complete the repeat breath-checking in the repeat breath-checking request step (S713). Thereafter, the breath-checking process in steps S704 and beyond described above may be executed in the same manner.

Figure 13:
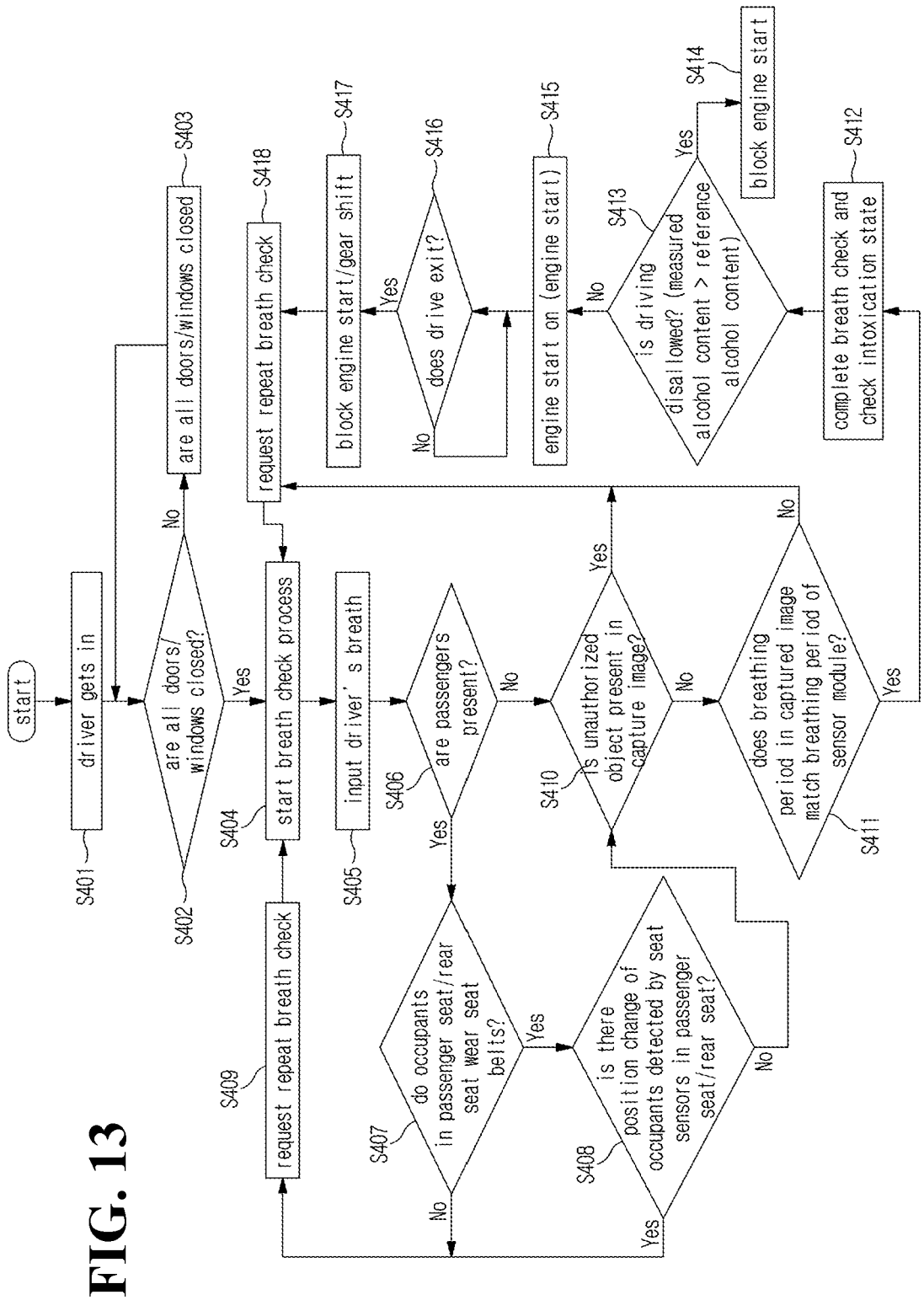
FIG. 13 is a flowchart of a drunk driving prevention method having an enhanced breath-checking process according to an embodiment of the present disclosure.

FIG. 13 is a flowchart of a drunk driving prevention method with an enhanced breath-checking method according to still another preferred embodiment of the present disclosure.

The embodiment of FIG. 13 differs from that of FIG. 11 in that the determination logic according to the presence of a passenger and the determination logic for the presence of an unauthorized object in the captured image are included. Other steps are substantially the same as the example described in FIG. 11.

As illustrated in FIG. 13, when the driver gets in the vehicle (S401), the check unit may start the breath-checking (S404).

At this time, the control module may check whether all doors and windows of the vehicle are closed before the breath-checking starts (S402). If some vehicle doors or windows are open, an instruction to close the open door/window may be issued through the display unit (S403).

If all doors/windows are closed, the breath-checking starts (S404).

Once the breath-checking starts, the sensor module pulls the breath exhaled by the driver and the step of receiving the driver's breath is executed (S405).

On the other hand, according to the present embodiment, a step of determining the presence of an unauthorized object in the captured image (S410) may be further executed before the breath validation step. In addition, the steps of determining whether passengers are present, whether the passengers wear the seat belts, and whether seat sensors sense a position change to determine whether the breath-checking is normal (S406 to S408) may be executed before determining the presence of an unauthorized object in the captured image.

FIG. 13 presupposed that steps S406 to S408 and S410 are all executed, but steps S406 to S407 may be omitted, and only step S410 may be executed in an embodiment of the present disclosure. Step S410 is a step of checking whether an unauthorized object other than the driver is present in the image captured by the camera before the breath validation step. When the presence of an unauthorized object is confirmed, the step of a repeat breath-checking request by the control module (S418) may be executed without entering the breath validation step.

Checking the presence of an unauthorized object in this step means checking the presence of an unauthorized object (a balloon or third party) other than the driver just in case (i) the driver gets in the vehicle alone with a balloon containing the breath of a third party and deceptively attempts the breath-checking using the balloon, or (ii) a third party gets in the vehicle in the vicinity of the driver and attempts the breath-checking deceptively.

Accordingly, the unauthorized object refers to an unauthorized object other than the driver and in-vehicle parts in the vicinity of the driver.

Figure 14:
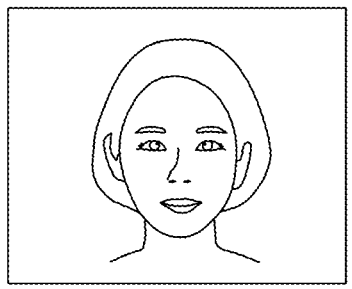
FIG. 14 is a view illustrating images captured by a camera during a breath-checking, (a) illustrating an image of a normal check attempt and (b) illustrating an image of an abnormal check attempt.
Figure 14:
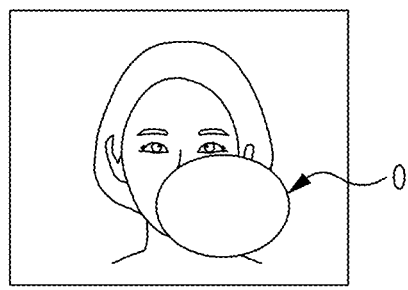

FIG. 14 illustrates an example of an unauthorized object compared with a normal image. FIG. 14A illustrates an image of a normal breath-checking attempt, and FIG. 14B illustrates an image of an abnormal breath-checking attempt (presence of an authorized object).

FIG. 14A illustrates a state of a normal breath-checking attempt with no cover on the face of the driver in the image captured by the camera during a normal breath-checking, while FIG. 14B illustrates a state of an abnormal breath-checking attempt with a balloon covering the face of the driver in the image captured during an abnormal breath-checking, in which case the image analysis unit confirms the presence of the unauthorized object and the check unit may refuse to complete the breath-checking.

On the other hand, in the example in which steps S406 to S408 and S410 are all executed, the step of checking the presence of passengers (S406) may be additionally executed before checking the presence of an unauthorized object.

When it is determined that passengers are present in step S406, whether the passengers in the passenger seat or rear seat all wear the seat belts is checked (S407). When any one of the passengers does not wear the seat belt, it is determined that there is a risk of a deceptive breath-checking attempt so that the completion of the breath-checking is denied and a repeat breath-checking is requested (S409). In contrast, when all passengers wear the seat belt, the step of detecting a position change of the passengers (S408) is executed. When it is confirmed that no passenger change positions, it is determined that no deceptive breath-checking is attempted and subsequence processes, preferably the step of checking the presence of an unauthorized object (S410) and the breath validation step (S411) may be sequentially executed. In contrast, when it is confirmed that any one of the passengers changes positions, it is determined that a deceptive breath-checking is attempted, in which case the completion of the breath-checking is denied and a repeat breath-checking is requested. (S409).

In addition, according to still another embodiment of the present disclosure, steps S406, S408, and S410 may be executed to the exclusion of the step of checking the seat belt wear (S407) only, in which case the step of detecting the position change of passengers (S408) may be executed instead of step S407 when the presence of passengers is confirmed.

After step S410 is normally completed, the breath validation step S411 of checking the match between the breathing period in the captured image and the breathing period of the sensor module from the received breath of the driver may be executed.

When it is determined that the breathing periods do not match in the breath validation step S411, the breath-checking is considered invalid, and a step of requesting a repeat breath-checking (S418) may be executed without completing the breath-checking.

In contrast, when it is determined that the breathing periods match in the breath validation step S411, the breath-checking is completed by the check unit of the control module and the step of checking the intoxication state by the determination unit is executed (S412). According to a preferred embodiment of the present disclosure, when the breath-checking is complete, the image information captured by the camera and the alcohol measurement information measured by the sensor module before the engine start may be stored in the storage unit.

Whether the alcohol content measured by the sensor module exceeds the preset reference alcohol content is determined when the intoxication state is checked (S413), and the engine start block device may be activated to block the engine start when the intoxicated driver is disallowed from driving the vehicle. When the control module determines that the measured alcohol content of the driver exceeds the reference alcohol content and that the driver is intoxicated, it is determined that the driver is too drunk to drive and the control module may transmit a control command to activate the engine start block device.

When no alcohol is detected in the exhaled breath of the driver or the alcohol content measured by the sensor module is equal to or less than the reference alcohol content, driving is considered allowed and the engine is started by turning on the ignition (S415).

On the other hand, after the control module completes the breath-checking, whether the validated driver leaves the vehicle while the engine is running is checked (S416), and the step of blocking the engine start and gear shift may be executed (S417) when it is determined that the driver leaves the vehicle after the vehicle is started. Since the driver is allowed to resume driving only after completing the repeat breath-checking when the engine start and gear shift are blocked, the driver may be informed in the repeat breath-checking request step S418 that the driver is required to complete the repeat breath-checking. The breath-checking process in steps S404 and beyond described above may be executed in the same manner after the repeat breath-checking request in steps S409 or S418.

A specific embodiment of the present disclosure is illustrated and described, but it will be obvious to those skilled in the art that the present disclosure may be improved upon and modified in various manners without deviating from the technical spirit of the present disclosure provided in the following claims.

What is claimed is:

1. A drunk driving prevention system comprising:
a camera configured to capture an image of a face of a driver seated in a driver's seat of a vehicle;
a sensor module configured to, during breath-checking of the driver, measure alcohol content in a breath exhaled from the driver; and
a control module configured to:
perform, based on the captured image, the breath-checking;
determine whether the breath-checking is completed,
determine, based on the measured alcohol content, whether the driver is intoxicated; and
determine, based on determining whether the driver is intoxicated, whether to block starting of an engine of the vehicle;
wherein the control module is configured to:
calculate a first estimated breathing period from a change to a shape of a mouth of the driver in the captured image; and
check whether a breath in the captured image matches a breath pulled into the sensor module based on a comparison between the first estimated breathing period and a second estimated breathing period determined from a change to a breath volume pulled in the sensor module to complete the breath-checking.

2. The drunk driving prevention system of claim 1, wherein:
the control module includes an image analysis unit configured to:
process and analyze the captured image; and
determine whether an unauthorized object other than the driver is present in the captured image, and
the control module is configured to, in response to determining that the unauthorized object is present in the captured image, determine that the breath-checking is incomplete.

3. The drunk driving prevention system of claim 1, wherein:
the control module includes a seat sensing unit configured to sense, using a plurality of seat sensors in passenger and rear seats of the vehicle, a presence of a plurality of passengers in the vehicle and a position change of the plurality of passengers, and
the control module is configured to determine that the breath-checking is incomplete when it is sensed that the plurality of passengers are present and the position change of the plurality of passengers is detected.

4. The drunk driving prevention system of claim 3, wherein:
the seat sensing unit is configured to determine whether each of the plurality of passengers is wearing a seat a belt, and
when it is sensed that at least one of the plurality of passengers is not wearing the seat belts, the control module is configured to determine that the breath-checking is incomplete.

5. The drunk driving prevention system of claim 3, wherein:
the seat sensing unit is configured to receive information on whether the driver leaves the vehicle; and
the control module is configured to transmit a control command to block engine start and gear shift in response to determining that the driver leaves the vehicle while the engine is running after completing the breath-checking.

6. The drunk driving prevention system of claim 1, wherein the control module includes:
a determination unit configured to determine whether the driver is intoxicated based on a comparison between the alcohol content measured by the sensor module with a reference alcohol content; and
a vehicle control unit configured to transmit a control command to activate an engine start block device in response to the determination unit determining that the driver is intoxicated.

7. The drunk driving prevention system of claim 1, further comprising a storage unit configured to store the captured image and the measured alcohol content.

8. The drunk driving prevention system of claim 1, wherein:
the control module includes a door sensing unit configured to detect opening and closing of all of a plurality of doors and windows of the vehicle;
in response to the door sensing unit detecting that at least one of the plurality of doors and windows being open, the door sensing unit is configured to transmit a control command to close the at least open one of the plurality of doors or windows.

9. The drunk driving prevention system of claim 1, wherein the control module is configured to determine that, in response to a ratio of a total time of the first estimated breathing period with respect to a total time of the second estimated breathing period being within a predetermined range, the breath in the captured image matches the breath pulled into the sensor module.

10. The drunk driving prevention system of claim 1, wherein, in response to (1) the second estimated breathing period being included in the first estimated breathing period, (2) a difference between a first start time of the second estimated breathing period and a second start time of the first estimated breathing period being less than a reference value, and (3) a first end time of the first estimated breathing period and a second end time of the second estimated breathing period being less than a reference value, the control module is configured to determine that the breath in the captured image matches the breath pulled into the sensor module.

* * * * *